(12) United States Patent
Martin et al.

(10) Patent No.: US 7,300,770 B2
(45) Date of Patent: Nov. 27, 2007

(54) DETECTION OF MICROBE CONTAMINATION ON ELASTOMERIC ARTICLES

(75) Inventors: Stephanie M. Martin, Woodstock, GA (US); John Gavin MacDonald, Decatur, GA (US); Allison Salyer Bagwell, Cumming, GA (US); Jason Lye, Atlanta, GA (US); Robert B. Johnson, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 39 days.

(21) Appl. No.: 11/117,635

(22) Filed: Apr. 28, 2005

(65) Prior Publication Data

US 2006/0134613 A1 Jun. 22, 2006

Related U.S. Application Data

(63) Continuation-in-part of application No. PCT/US2004/04261, filed on Dec. 16, 2004.

(51) Int. Cl.
*C12Q 1/22* (2006.01)

(52) U.S. Cl. .............................. 435/31; 436/1; 2/161.7; 264/78

(58) Field of Classification Search ................... 435/31
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,705,032 A | 12/1972 | Honjo et al. | |
| 3,802,817 A | 4/1974 | Matsuki et al. | |
| 3,849,241 A | 11/1974 | Butin et al. | |
| 4,100,324 A | 7/1978 | Anderson et al. | |
| 4,310,928 A | 1/1982 | Joung | |
| 4,340,395 A | 7/1982 | Magers et al. | |
| 4,340,563 A | 7/1982 | Appel et al. | |
| 4,375,448 A | 3/1983 | Appel et al. | |
| 4,494,278 A | 1/1985 | Kroyer et al. | |
| 4,511,488 A | 4/1985 | Matta | |
| 4,556,636 A | 12/1985 | Belly et al. | |
| 4,640,810 A | 2/1987 | Laursen et al. | |
| 4,677,076 A | 6/1987 | Langhals | |
| 4,775,582 A | 10/1988 | Abba et al. | |
| 4,780,422 A | 10/1988 | Mitani et al. | |
| 4,818,464 A | 4/1989 | Lau | |
| 4,833,003 A | 5/1989 | Win et al. | |
| 4,853,281 A | 8/1989 | Win et al. | |
| 5,036,000 A | 7/1991 | Palmer et al. | |
| 5,112,900 A | 5/1992 | Buddenhagen et al. | |
| 5,407,715 A | 4/1995 | Buddenhagen et al. | |
| 5,464,739 A | 11/1995 | Johnson et al. | |
| 5,468,469 A | 11/1995 | Aszalos et al. | |
| 5,527,171 A | 6/1996 | Soerensen | |
| 5,534,416 A | 7/1996 | Millard et al. | |
| 5,742,943 A | 4/1998 | Chen | |
| 5,744,321 A | 4/1998 | Harewood | |
| 5,792,531 A | 8/1998 | Littleton et al. | |
| 5,900,452 A | 5/1999 | Plamthottam | |
| 6,090,541 A | 7/2000 | Wicks et al. | |
| 6,168,655 B1 | 1/2001 | Nohr et al. | |
| 6,288,159 B1 | 9/2001 | Plamthottam | |
| 6,306,514 B1 | 10/2001 | Weikel et al. | |
| 6,362,006 B1 * | 3/2002 | Potyrailo et al. | ........... 436/131 |
| 6,368,558 B1 | 4/2002 | Suslick et al. | |
| 6,383,815 B1 | 5/2002 | Potyrailo | |
| 6,524,846 B1 * | 2/2003 | Robinson, Jr. | ........... 435/287.4 |
| 2003/0119202 A1 | 6/2003 | Kaylor et al. | |
| 2003/0143112 A1 | 7/2003 | Suslick et al. | |
| 2003/0198573 A1 | 10/2003 | Forood et al. | |
| 2005/0130253 A1 | 6/2005 | Lye et al. | |
| 2006/0134613 A1 | 6/2006 | Martin et al. | |
| 2006/0134728 A1 | 6/2006 | MacDonald et al. | |

FOREIGN PATENT DOCUMENTS

| | | | |
|---|---|---|---|
| EP | 0266196 | * | 4/1988 |
| EP | 0266196 A2 | | 5/1988 |
| EP | 0266196 A3 | | 5/1988 |
| EP | 0517050 A2 | | 5/1992 |
| EP | 0 846 767 A | | 6/1998 |
| GB | 1107790 | | 3/1968 |
| GB | 2178847 A | | 2/1987 |

(Continued)

OTHER PUBLICATIONS

Zachariasse KA et al (1981) Investigation of micelles, microemulsions, and phospholipid bilayers with the pyrdinium N-phenolbetaine ET(30), a polarity probe for aqueous solutions. J Phys Chem, vol. 85, pp. 2676-2683.*
Search Report and Written Opinion for PCT/US2005/038415, Jul. 27, 2006.
Search Report and Written Opinion for PCT/US2005/038416.
Abstract of Japanese Patent No. JP11083849 with XP-002327939, Mar. 26, 1999.
Abstract of Article—*A $^1H$ NMR Investigation Concerning the Insertion of Pyridinium N-Phenoxide Betaines into Micelles*, Plieninger et al., Liebigs Ann. Chem. 1983, pp. 860-875.

(Continued)

*Primary Examiner*—Jon Weber
*Assistant Examiner*—Clark D. Petersen
(74) *Attorney, Agent, or Firm*—Dority & Manning, P.A.

(57) ABSTRACT

An elastomeric article that contains a chromogen that undergoes a detectable change in color in the presence of one or more microbes is provided. For example, in one embodiment, the chromogen is a solvatochromic dye (e.g., Reichardt's dye) that undergoes a color change in the presence of bacteria or other microbes. More specifically, such dyes may respond to differences in polarity between microbe components (e.g., cell membrane, cytoplasm, etc.) and the environment outside the cell. Alternatively, other mechanisms may be wholly or partially responsible for the interaction between the dye and the microbe, such as acid-base reactions, redox reactions, and so forth.

12 Claims, 4 Drawing Sheets

FOREIGN PATENT DOCUMENTS

| WO | WO 9730341 A1 | 8/1997 |
| --- | --- | --- |
| WO | WO 0233413 A1 | 4/2002 |
| WO | WO 02103356 A1 | 12/2002 |
| WO | WO 2005/016230 A | 2/2005 |
| WO | WO 2005/059162 A | 6/2005 |

OTHER PUBLICATIONS

Article—*Colour and Constitution of Organic Molecules*, John Griffiths, Academics Press, 1976, pp. 16-80 and pp. 146-160.

Article—*Solvent dependent hyperpolarizability of a merocyanine dye*, Levine et al., J. Chem. Phys., vol. 68, No. 11, Jun. 1, 1978, pp. 5042-5045.

Article—*Investigation of Micelles, Microemulsions, and Phospolipid Bilayers with the Pyridinium N-Phenolbetaine Er(30), a Polarity Probe for Aqueous Interfaces*, Zachariasse et al., J. Phys. Chem., vol. 85, No. 18, Sep. 3, 1981, pp. 2676-2683.

Article—*Synthesis and structure-property relationships of amphiphilic acidochromic hydroxystilbazolium dyes*, Lehmann et al., Sensors and Actuators B 38-39, 1997, pp. 229-234.

Article—*Second order hyperpolarizability of hydroxystilbazolium salts and their betaines—relationship to chemical structure*, Grummt et al., J. Mater. Chem., vol. 9, 1999, pp. 1419-1424.

Article—*Nile Red: A Selective Fluorescent Stain for Intracellular Lipid Droplets*, Greenspan et al., The Journal of Cell Biology, vol. 100, Mar. 1985, pp. 965-973.

Article—*Pyridinium N-phenolate betaine dyes as empirical indicators of solvent polarity: Some new findings*, Reichardt, Pure Appl. Chem., vol. 76, No. 10, 2004, pp. 1903-1919.

Pocket Guide to Digital Printing, Frank Cost, Delmar Publishers, Albany, NY, ISBN 0-8273-7592-1, pp. 144-145, 1997.

Article—*Potential Antitumor Phenoxazines*, Motohashi et al., Medicinal Research Reviews, vol. 11, No. 3, May 1991, pp. 239-294.

Article—The Change in Research for the Therapy of Tumors, Sedlacek et al., Chimia, vol. 45, No. 10, Oct. 1991, pp. 311-316.

Chapters 6 and 9-11 from book entitled Photodynamic Action and Diseases Caused by Light by Harold Francis Blum, American Chemical Society Series of Scientific and Technologic Monographs, 1941.

Article—Rapid Diagnosis of Adenoviral Keratoconjunctivitis by a Fully Automated Molecular Assay, Koidl et al., Ophthalmology, vol. 112, No. 9, Sep. 2005, pp. 1521.e1-1521.e8.

Article—Simplifying Collection of Corneal Specimens in Cases of Suspected Bacterial Keratitis, Kaye et al., Journal of Clinical Microbiology, vol. 41, No. 7, Jul. 2003, pp. 3192-3197.

Article—Development and Use of Nested Polymerase Chain Reaction (PCR) for the Detection of Adenovirus from Conjunctivitis Specimens, Dalapathy, et al., Journal of Clinical Virology 11, 1998, pp. 77-84.

Article—Chloramphenicol Treatment for Acute Infective Conjunctivitis in Children in Primary Care: A Randomised Double-Blind Placebo-Controlled Trial, Rose et al., The Lancet, vol. 366, Jul. 2, 2005, pp. 37-43.

Standard Practice for Obtaining Spectrometric Data for Object-Color Evaluation, ASTM International, E-1164, 2002, pp. 1-8.

Paints and Varnishes—Colorimetry—Part 1: Principles, International Standard ISO 7724/1-1984 (E), Oct. 1, 1984.

Methods of Colour Measurement—Reflecting and Transmitting Objects, Japanese Industrial Standard, JIS Z 8722:2000 (E).

Colorimetry, 2nd Edition, International Commission on Illumination, No. 15.2, 1986.

Article—Ocular Virulence of Capsule-Deficient *Streptococcus pneumoniae* in *Rabbit keratitis* Model, Reed et al., Investigative Ophthalmology & Visual Science, Feb. 2005, vol. 46, No. 2, pp. 604-608.

Abstract of Detection of Adenovirus DNA in Clinical Samples by SYBR Green Real-Time Polymerase Chain Reaction Assay, Watanabe et al, Jun. 2005.

Abstract of Antimicrobial Resistance Among Clinical Isolates of *Haemophilus influenzae* in Northern Italy. Vollaborative Study on Pediatric Infectious Diseases, Garlaschi, et al, Jan. 1993.

\* cited by examiner

R=CH3- , CH3(CH2)4CH2-, CH3(CH2)10CH2-, CH3(CH2)20CH2-

7.7g(0.083mole)   12.9g(0.09mole)     Theo.  19.6g
                                      Act    18.6g(crude)

DETECTION OF MICROBE CONTAMINATION ON ELASTOMERIC ARTICLES

RELATED APPLICATIONS

The present application is a continuation-in-part application of International Application No. PCT/US2004/042461, filed on Dec. 16, 2004, which claims priority to U.S. patent application Ser. No. 10/737,574, filed on Dec. 16, 2003.

BACKGROUND OF THE INVENTION

Microbial contamination of elastomeric articles is problematic in many applications. For example, in medical applications (e.g., surgery), microbial contamination of the elastomeric gloves worn by medical personnel is particularly dangerous due to the increased likelihood of infection and the potential for spreading infection to a large number of patients and/or other medical personnel. Thus, several steps are generally taken to ensure that the gloves are free of bacteria and other microbes. During surgery, for instance, a surgeon scrubs his/her hands with a strong bactericidal soap and a brush or sponge to eliminate the presence of inimical microbes. The surgeon then dons presterilized gloves and performs the procedure. In some cases, however, one or more portions of the glove may still become contaminated with microbes. For example, the surgeon may inadvertently contact a contaminated surface during the procedure. Likewise, microbes present deep within in the pores of the skin may reinfest the hands after donning, and thus create a hazard to the patient if the integrity of the glove becomes compromised, such as when the gloves are snagged during donning or punctured by an instrument or a bone fragment.

Besides medical applications, elastomeric articles are also used in other applications in which microbe contamination is of concern. For example, personnel who handle food products (e.g., meat) often wear elastomeric gloves to inhibit microbe contamination. However, the possibility remains that the elastomeric articles will inadvertently contact foodborne pathogens, such as *Salmonella* and *Listeria*. If undetected, these pathogens will multiply to an undesirable level during the packaging, transportation, and display of the product. For instance, a temperature increase of less than 3° C. may shorten food shelf life by 50% and cause a significant increase in bacterial growth over time. Indeed, spoilage of food may occur in as little as several hours at 37° C. based on a total pathogenic and non-pathogenic bacterial load of $10^3$ colony forming units ("cfu") per gram on food products.

As such, a need currently exists for a technique of readily detecting the presence of microbes on elastomeric articles.

SUMMARY OF THE INVENTION

In accordance with one embodiment of the present invention, an elastomeric article is disclosed that comprises an elastomeric material and a microbe-sensitive chromogen. The microbe-sensitive chromogen (e.g., a solvatochromic dye) is present in an amount effective to undergo a detectable color change in the presence of one or more microbes.

In accordance with another embodiment of the present invention, a method for determining the presence of one or more microbes on an elastomeric article is disclosed. The method comprises applying a treatment composition to the elastomeric article, the treatment composition comprising a chromogen and a carrier. Thereafter, the chromogen is contacted with one or more microbes so that the chromogen undergoes a detectable color change.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
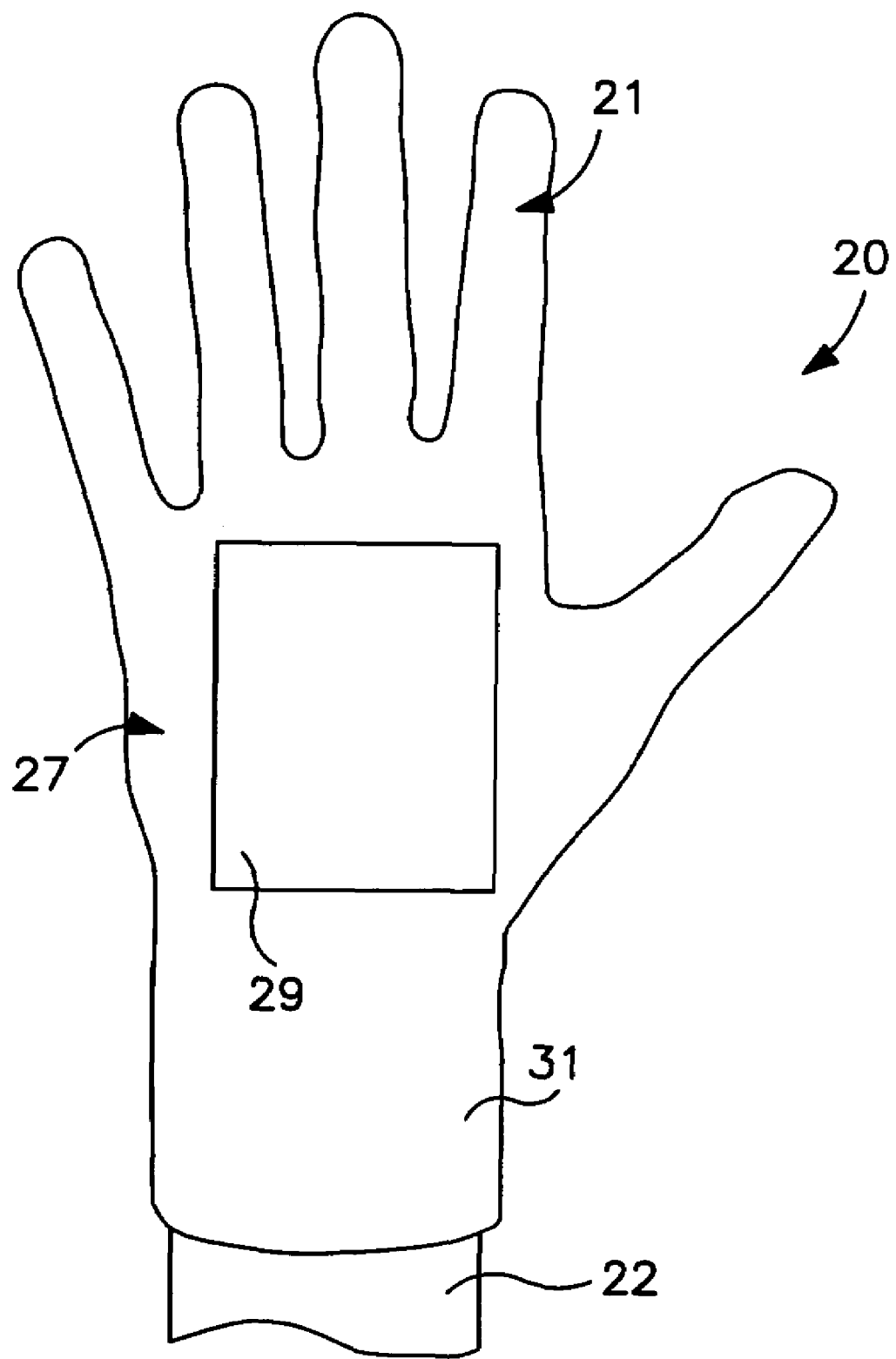
FIG. 1 is a perspective view of one embodiment of an elastomeric glove made according to the invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to an elastomeric article that contains a chromogen that undergoes a detectable change in color in the presence of one or more microbes. For example, in one embodiment, the chromogen is a solvatochromic dye (e.g., Reichardt's dye) that undergoes a color change in the presence of bacteria or other microbes. More specifically, such dyes may respond to differences in polarity between microbe components (e.g., cell membrane, cytoplasm, etc.) and the environment outside the cell. Alternatively, other mechanisms may be wholly or partially responsible for the interaction between the dye and the microbe, such as acid-base reactions, redox reactions, and so forth.

I. Elastomeric Articles

Any of a variety of elastomeric articles may be incorporated with the chromogen in accordance with the present invention. For example, gloves and condoms, as well as medical devices, such as dilatation balloons, inflatable cuffs, external catheters, catheter balloons, instrument covers, and so forth, may be utilized in the present invention. The elastomeric article typically contains an elastomeric material formed from an elastomeric material, such as natural rubber latex, isoprene polymers, chloroprene polymers, vinyl chloride polymers, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, butadiene polymers, styrene-butadiene polymers, carboxylated styrene-butadiene polymers, acrylonitrile-butadiene polymers, carboxylated acrylonitrile-butadiene polymers, acrylonitrile-styrene-butadiene polymers, carboxylated acrylonitrile-styrene-butadiene polymers, derivatives thereof, and so forth. Suitable S-EB-S block copolymers, for instance, are described in U.S. Pat. No. 5,112,900 to Buddenhagen, et al.; U.S. Pat. No. 5,407,715 to Buddenhagen, et al.; U.S. Pat. No. 5,900,452 to Plamthottam; and U.S. Pat. No. 6,288,159 to Plamthottam, which are incorporated herein in their entirety by reference thereto for all purposes.

The elastomeric article may be single- or multi-layered. For example, the article may include a coating that overlies at least a portion of the elastomeric material. In one particular embodiment, a donning layer may be used to facilitate the insertion of an elastomeric glove over a user's hand. Some examples of suitable materials for the donning layer include, but are not limited to, polybutadienes (e.g., syndiotactic 1,2 polybutadiene), polyurethanes, block copolymers, and so forth. Other examples of such polymers are described in U.S. Pat. No. 5,792,531 to Littleton, et al., which is incorporated herein in its entirety by reference thereto for all purposes. A lubricant may also coat the donning layer to further aid in wet and/or dry lubricity. The lubricant, for example, may include a cationic surfactant (e.g., cetyl pyridinium chloride), an anionic surfactant (e.g., sodium lauryl sulfate), a nonionic surfactant (e.g., polyethylene glycol), and so forth. The lubricant may also contain a silicone emulsion, such as DC 365 (Dow Corning) or SM 2140 (GE Silicones).

An elastomeric article made in accordance with the present invention may generally be formed using a variety of processes known in the art. For example, elastomeric article formation techniques may utilize dipping, spraying, chlorination, drying, curing, as well as any other technique known in the art. Some examples of suitable methods for forming an elastomeric article that may be used in the present invention are described in U.S. Pat. No. 5,112,900 to Buddenhagen, et al.; U.S. Pat. No. 5,407,715 to Buddenhagen, et al.; U.S. Pat. No. 5,742,943 to Chen; U.S. Pat. No. 5,792,531 to Littleton, et al.; U.S. Pat. No. 5,900,452 to Plamthottam; U.S. Pat. No. 6,288,159 to Plamthottam; and U.S. Pat. No. 6,306,514 to Weikel, et al., which are incorporated herein in their entirety by reference thereto for all purposes.

For instance, in some embodiments, a former having the shape of the article, such as a hand shape for an elastomeric glove, is initially dipped into a bath containing a coagulant for an elastomeric material. The bath may also include other optional ingredients, such as a surfactant, water, a salt that contains calcium ions (e.g., calcium nitrate and/or calcium carbonate), and so forth. The salt, for instance, may break the protection system of natural rubber latex emulsions and also facilitate removal of the tacky latex from the former, thus acting as a release agent. The surfactant may provide good wetting to avoid forming a meniscus and trapping air between the form and deposited latex, particularly in the cuff area. If desired, the former may be preheated so that the residual heat dries off the water leaving, for example, calcium nitrate, calcium carbonate, and surfactant on the surface of the former. Other suitable coagulant solutions are also described in U.S. Pat. No. 4,310,928 to Joung, which is incorporated herein in its entirety by reference thereto for all purposes.

After being immersed in the coagulant composition, the former is withdrawn and allowed to dry. The former may then be dipped into a tank containing an elastomeric polymer bath to form the substrate body. The bath contains, for example, natural rubber latex, stabilizers, antioxidants, curing activators, organic accelerators, vulcanizers, and so forth. The former is dipped into one or more latex baths a sufficient number of times to build up the desired thickness on the former. By way of example, the substrate body may have a thickness of from about 0.1 to about 0.3 millimeters. If a glove is being formed, a bead roll station may be utilized to impart a cuff thereto. The latex-coated former is then dipped into a leaching tank in which hot water is circulated to remove the water-soluble components, such as residual calcium nitrates and proteins contained in the natural latex. This leaching process may continue for about twelve minutes with the tank water being about 49° C. The article may then be optionally dipped into a solution to form a coating. Once coated, the former is sent to a curing station (e.g., oven) where the latex is vulcanized or cured. The elastomeric article may then be applied with various other treatment compositions (e.g., lubricant, halogenation, etc.), either "off-line" (i.e., after stripping) or "on-line"

II. Microbe-Sensitive Chromogens

Generally speaking, the microbe-sensitive chromogen employed in the present invention possesses the ability to signal the presence of one or more microbes. Any of a variety of different types of microbes may generally be detected in accordance with the present invention, such as bacteria, fungi, viruses, mold, yeast, etc. For example, the microbe-sensitive chromogens of the present invention may detect bacteria of a variety of different shapes, cell arrangements, and compositions. Most bacteria, for instance, have one of five basic cell shapes, i.e., (1) round or cocci, (2) rod or bacilli, (3) spiral or spirilli, (4) comma or vibrios, and (5) filaments. Likewise, examples of possible cell arrangements include diplococci (e.g., pair), streptococci (e.g., chain), and staphylococci (e.g., bunched). Diplococci, for example, are known to cause pneumonia. Streptococci are often associated with "strep throat." Staphylococci are familiar to many because of their role in "staph infections" and some types of food poisoning. Bacteria also vary somewhat in size, but generally average about $\frac{1}{25,000}$ inch (2.54 cm) per bacteria. In some cases, the shape or cell arrangement may impact the sensitivity of a particular chromogen for the microbe.

Although bacteria generally contain cell membranes (i.e., walls) made from lipid bi-layers of liposaccharides, the composition of a type of bacteria may be more specifically classified using a Gram reaction (a staining method to classify bacteria). For example, gram-positive bacteria retain crystal violet stain in the presence of alcohol or acetone and include, for instance, the genera *Actinomyces, Bacillus, Bifidobacterium, Cellulomonas, Clostridium, Corynebacteriumk, Micrococcus, Mycobacterium, Nocardia, Staphylococcus, Streptococcus* and *Streptomyces*. Some of the Gram-positive bacteria notably those of the genera *Corynebacterium, Mycobacterium* and *Nocardia* retain dyes even in the presence of acid. These are known as Acid-Fast bacteria. Gram-negative bacteria do not retain crystal violet stain in the presence of alcohol or acetone, and include, for instance, the genera *Acetobacter, Agrobacterium, Alcaligenes, Bordetella, Brucella, Campylobacter, Caulobacter, Enterobacter, Erwinia, Escherichia, Helicobacterium, Legionella, Nesseria, Nitrobact, Pasteurelia, Pseudomonas, Rhizobium, Rickettsia, Salmonella, Shigella, Thiobacilus, Veiellonealla, Vibrio, Xanthomonas* and *Yersinia*.

Gram-negative cell membranes include lipopolysaccharides as a main component, and additionally include phospholipids, proteins, lipoproteins, and small amounts of peptidoglycans. The lipopolysaccharide component has a core region to which are attached repeating units of polysaccharide moieties or side chains. The chemical composition of these side chains, both with respect to composition and arrangement of the different sugars, determines the nature of the somatic or O antigen determinants. Such determinants, in turn, are useful in serologically classifying many gram-negative species. For example, some types of gram-negative bacteria that belong to quite different species and have strong serological cross-reactivity, nevertheless possess chemically similar carbohydrate moieties as part of their lipopolysaccharide side chains, which generally have about 30 repeating units. The cell membranes of gram-positive bacteria include peptidoglycans, polysaccharides, and/or teichoic acids. The peptidoglycans (also called "murein") are heteropolymers of glycan strands and are cross-linked through short peptides. The bases of the murein are chains of alternating residues of N-acetylglucosamine and N-acetyl muramic acid, which are β-1,4-linked. These chains are cross-linked by short polypetide chains containing both L- and D-amino acids.

Despite sharing common features, the arrangement and composition of the surfaces of gram-positive and gram-negative bacteria nevertheless differ. For example, gram-negative bacteria have an outer membrane coated with lipopolysaccharide (LPS). The LPS lends a net-negative charge to the surface of gram-negative bacteria and contributes to its pathogenesis. Gram-positive bacteria, on the other hand, are coated with thick peptidoglycan (or murein) sheet-like layers. The sheets are formed from alternating N-acetyl-glucosamine and N-acetylmuramic acid molecules. Teichoic acids are also found in gram-positive bacteria and may be linked to the N-acetylmuramic acid. While gram-negative bacteria also have peptidoglycan, the layer on gram-positive bacteria is much thicker. The peptidoglycan layer of gram-negative bacteria is also located underneath the LPS layer, making it less accessible from the surface.

In addition to bacteria, other microbes of interest include molds and yeasts (e.g., *Candida albicans*), which belong to the Fungi kingdom. Zygomycota, for example, is a class of fungi that includes black bread mold and other molds that exhibit a symbiotic relationship with plants and animals. These molds are capable of fusing and forming tough "zygospores." Ascomycota is another class of fungi, which includes yeasts, powdery mildews, black and blue-green molds, and some species that cause diseases such as Dutch elm disease, apple scab, and ergot. The life cycle of these fungi combines both sexual and asexual reproduction, and the hyphae are subdivided into porous walls that allow for passage of the nuclei and cytoplasm. Deuteromycota is another class of fungi that includes a miscellaneous collection of fungi that do not fit easily into the aforementioned classes or the Basidiomycota class (which includes most mushrooms, pore fungi, and puffball fungi). Deuteromycetes include the species that create cheese and penicillin, but also includes disease-causing members such as those that lead to athlete's foot and ringworm.

Regardless of the type of microbe of interest, a microbe-sensitive chromogen may be selected in accordance with the present invention that interacts in some manner with the cell membrane of the microbe and/or the environment in which the microbe is present. As a result of this interaction, the chromogen undergoes a change in color that is readily detectable (e.g., with an unaided eye). The term "color" relates to the presence or absence of certain wavelengths of light reflected or emitted from objects in a visual field. Light entering the eye, for example, is subjected to a spectral analysis by three types of retinal cone cells that are sensitive to specific regions of the visible spectrum. Stimuli from these cells are in turn processed by retinal neurons, optic nerve neurons and the visual cortex so that a sensation of color is experienced. The chromogen employed in the present invention typically owes its color to the absorption of certain wavelengths of light. As such, the perceived color is usually the complement of the color associated with the wavelength of light being absorbed by the object. An object that appears to be red in color when viewed in white light, for example, is in fact selectively absorbing bluish light in the wavelength range of 490 to 500 nanometers. Similarly, an object that appears yellow in white light is in fact absorbing blue light in the wavelength range of 435 to 480 nanometers.

The absorption of visible light is associated with electronic transitions within a molecule and results in the generation of an excited state. The energy difference between the ground state of the molecule and the relevant excited state determines the wavelength of the light absorbed according to the Planck relationship:

$$E = h\nu$$

wherein,

E is energy, h is Planck's constant, and $\nu$ is the frequency of the photon of light absorbed, and is related to wavelength $\lambda$ and the speed of light c by $\nu = c/\lambda$.

A state diagram, such as shown below, may be used to graphically depict electronic transitions:

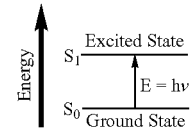

The energy of an absorbed photon is thus inversely proportional to the wavelength of the photon. Thus, photons of blue light (435-480 nanometers) have a higher energy than yellow light (580-595 nanometers). As such, the color of the chromogen is determined by the transition energy between the ground state of the chromogen and the first allowed excited state.

The light-absorbing portion of the chromogen employed in the present invention is a chromophore that is generally responsible for the color of the chromogen and is connected to a conjugated system. For instance, azo groups (e.g., azo dyes), polyene groups (e.g., carotene dye), carbonyl groups (e.g., anthraquinone dyes) are common chromophores. Auxochromes may induce a shift of the absorption maxima of the chromophore towards either the red end of the spectrum ("bathochromic shift") or the blue end of the spectrum ("hypsochromic shift"). Auxochromes may or may not be conjugated with the chromogen. For instance, an amino group conjugated to an azo group (chromophore) via, for instance, a benzene ring, will form an aminoazo chromogen. The type of absorption shift depends on the nature of the chromophore and, for example, on whether the auxochrome functions as an electron acceptor, in which a hypsochromic shift results, or whether the amino group functions as an electron donor, in which a bathochromic shift results. For example, a conjugated amino auxochrome will shift the absorption band of the azo group to longer wavelengths and increases the intensity of the absorption band. The absorption shift provides a color difference that is detectable, either visually or through instrumentation.

One particularly suitable class of chromogens that may undergo a detectable color change in the presence of one or more microbes is solvatochromic dyes. Solvatochromic dyes are dyes having spectroscopic characteristics (e.g., absorption) in the ultraviolet/visible/near-infrared spectrum and are sometimes influenced by the surrounding medium. The solvatochromic dyes may be positive or negative, which corresponds to bathochromic and hypsochromic shifts, respectively, of the emission band with increasing solvent polarity. In one embodiment, for instance, the solvatochromic dye undergoes a color change in a certain molecular environment based on solvent polarity and/or hydrogen bonding propensity. For example, a solvatochromic dye may be blue in color in a polar environment (e.g., water), but yellow or red in a non-polar environment (e.g., lipid-rich solution). The color produced by the solvatochromic dye depends on the molecular polarity difference between the ground and excited state of the dye.

Merocyanine dyes (e.g., mono-, di-, and tri-merocyanines) are one example of a type of solvatochromic dye that may be employed in the present invention. Merocyanine dyes, such as merocyanine 540, fall within the donor—simple acceptor chromogen classification of Griffiths as discussed in "Colour and Constitution of Organic Molecules" Academic Press, London (1976). More specifically, merocyanine dyes have a basic nucleus and acidic nucleus separated by a conjugated chain having an even number of methine carbons. Such dyes possess a carbonyl group that acts as an electron acceptor moiety. The electron acceptor is conjugated to an electron donating group, such as a hydroxyl or amino group. The merocyanine dyes may be cyclic or acyclic (e.g., vinylalogous amides of cyclic merocyanine dyes). For example, cyclic merocyanine dyes generally have the following structure:

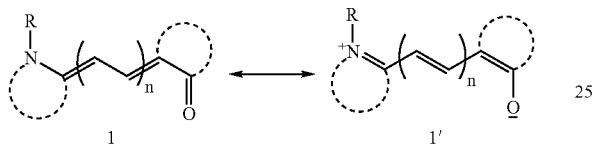

wherein, n is any integer, including 0. As indicated above by the general structures 1 and 1', merocyanine dyes typically have a charge separated (i.e., "zwitterionic") resonance form. Zwitterionic dyes are those that contain both positive and negative charges and are net neutral, but highly charged. Without intending to be limited by theory, it is believed that the zwitterionic form contributes significantly to the ground state of the dye. The color produced by such dyes thus depends on the molecular polarity difference between the ground and excited state of the dye. One particular example of a merocyanine dye that has a ground state more polar than the excited state is set forth below as structure 2.

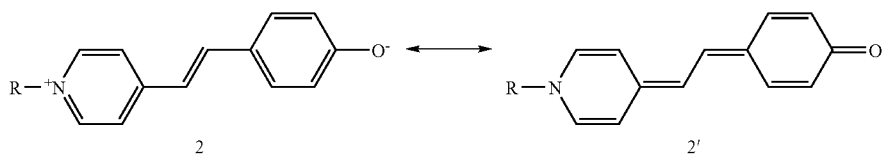

The charge-separated left hand canonical 2 is a major contributor to the ground state whereas the right hand canonical 2' is a major contributor to the first excited state. Still other examples of suitable merocyanine dyes are set forth below in the following structures 3-13.

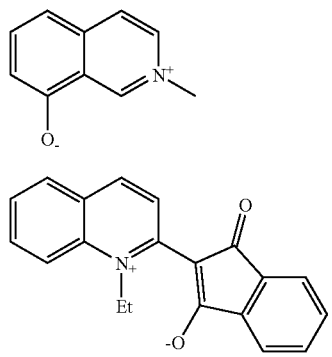

-continued

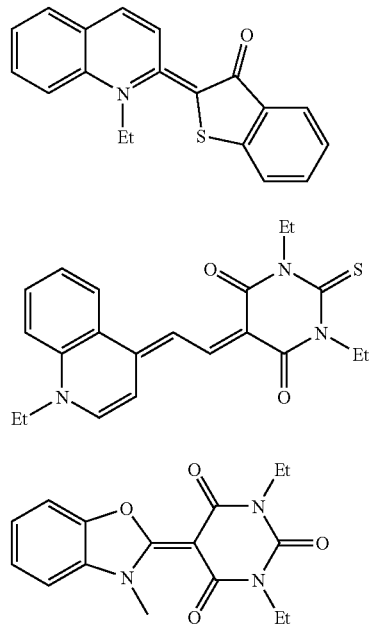

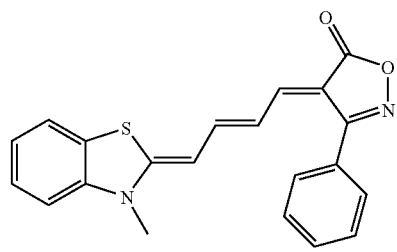

-continued

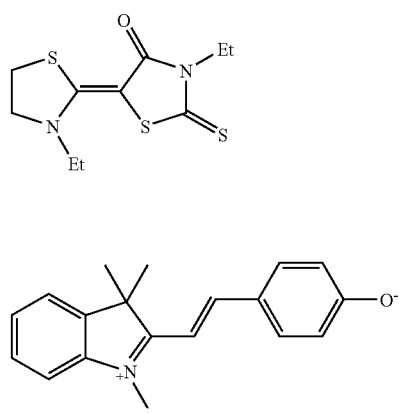

-continued

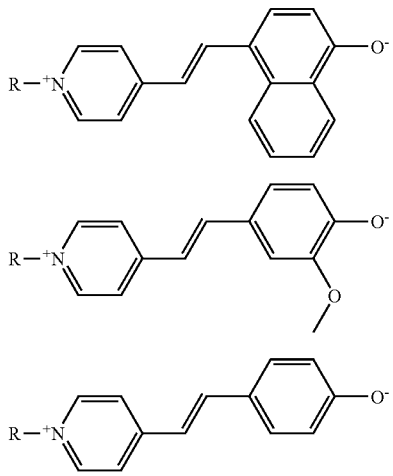

11

12

13 wherein, "R" is a group, such as methyl, alkyl, aryl, phenyl, etc.

Indigo is another example of a suitable solvatochromic dye for use in the present invention. Indigo has a ground state that is significantly less polar than the excited state. For example, indigo generally has the following structure 14:

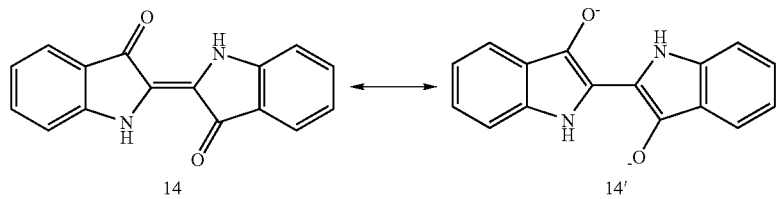

14      14'

The left hand canonical form 14 is a major contributor to the ground state of the dye, whereas the right hand canonical 14' is a major contributor to the excited state.

Other suitable solvatochromic dyes that may be used in the present invention include those that possess a permanent zwitterionic form. That is, these dyes have formal positive and negative charges contained within a contiguous π-electron system. Contrary to the merocyanine dyes referenced above, a neutral resonance structure cannot be drawn for such permanent zwitterionic chromogens. Exemplary dyes of this class include betaine dyes, such as 4-(2,4,6-triphenylpyridinium-1-yl)-2,6-diphenylphenolate (Reichardt's dye) having the following general structure 15.

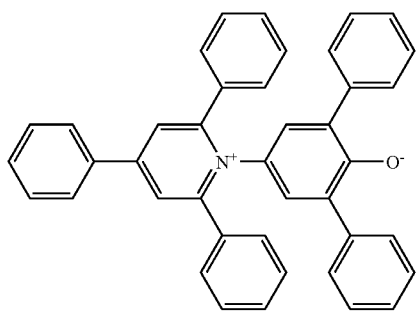

15

Reichardt's dye shows strong negative solvatochromism. That is, Reichardt's dye displays a shift in absorbance to a shorter wavelength and thus has visible color changes as solvent eluent strength (polarity) increases. Still other examples of suitable negatively solvatochromic pyridinium N-phenolate betaine dyes are set forth below in structures 16-22:

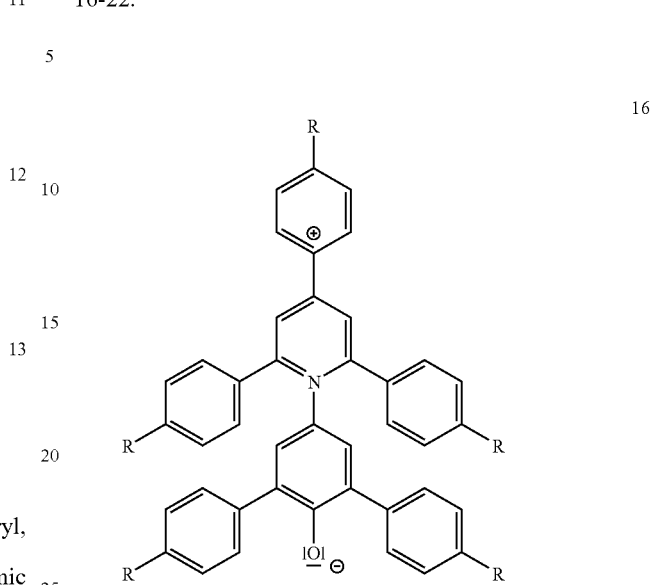

16 wherein, R is hydrogen, —C(CH$_3$)$_3$, —CF$_3$, or C$_6$F$_{13}$.

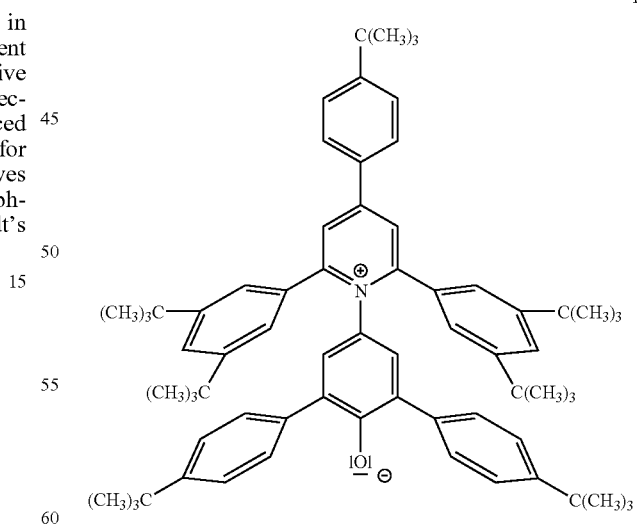

17

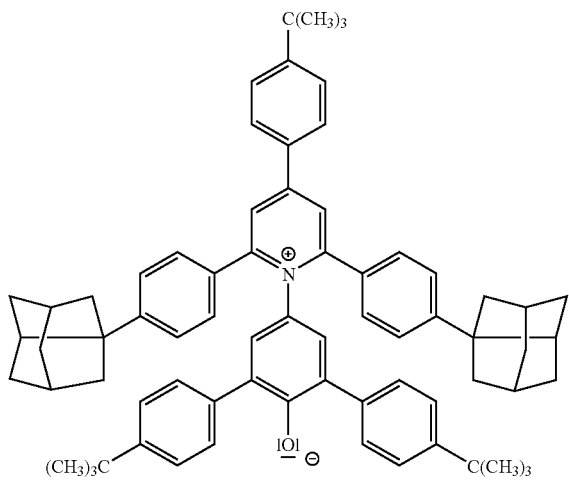
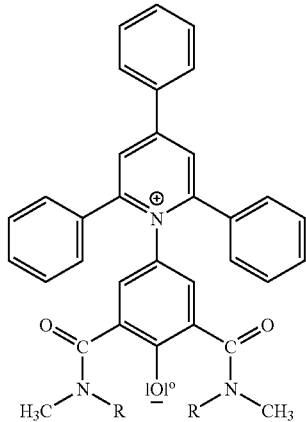
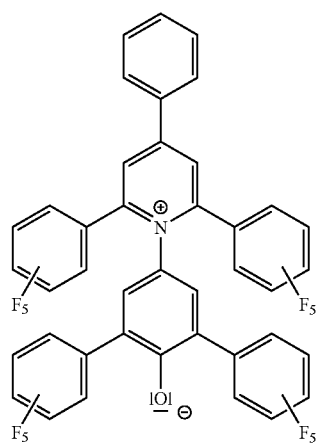
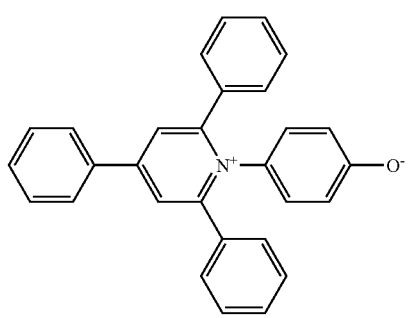
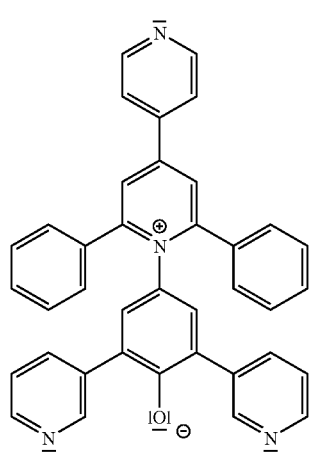
Still additional examples of dyes having a permanent zwitterionic form include dyes having the following general structure 23:
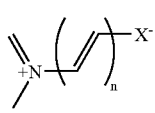
wherein, n is 0 or greater, and X is oxygen, carbon, nitrogen, sulfur, etc. Particular examples of the permanent zwitterionic dye shown in structure 23 include the following structures 24-32.
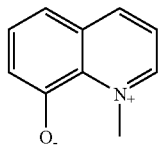

-continued

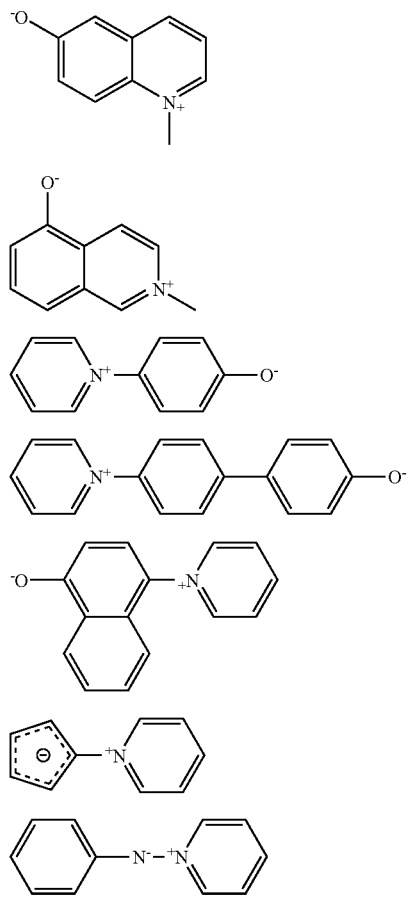

Still other suitable solvatochromic dyes may include, but are not limited to 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl) julolidine (DCVJ); phenol blue; stilbazolium dyes; coumarin dyes; ketocyanine dyes; N,N-dimethyl-4-nitroaniline (NDMNA) and N-methyl-2-nitroaniline (NM2NA); Nile blue; 1-anilinonaphthalene-8-sulfonic acid (1,8-ANS), and dapoxylbutylsulfonamide (DBS) and other dapoxyl analogs. Besides the above-mentioned dyes, still other suitable dyes that may be used in the present invention include, but are not limited to, 4-[2-N-substituted-1,4-hydropyridin-4-ylidine)ethylidene]cyclohexa-2,5-dien-1-one, red pyrazolone dyes, azomethine dyes, indoaniline dyes, and mixtures thereof.

Although the above-referenced dyes are classified as solvatochromic, it should be understood that the present invention is not necessarily limited to any particular mechanism for the detectable color change of the chromogen in the presence of a microbe. For example, even when a solvatochromic dye is employed, other mechanisms may actually be wholly or partially responsible for the color change of the dye in the presence of a microbe. For example, acid-base or proton donation reactions between the dye and microbe may result in the color change. As an example, highly organized acid moieties on bacteria cell walls may protonate certain dyes, resulting in a loss of color. Redox reactions between the dye and microbe may likewise contribute to the color change.

III. Application to Elastomeric Article

The chromogen may generally be applied to the elastomeric article according to any technique known in the art. In some embodiments, the chromogen is incorporated into a treatment composition to facilitate its application to an elastomeric article. The nature of the treatment composition may vary depending on the nature of the chromogen, elastomeric article, application technique, etc. For example, the treatment composition may contain a carrier for the chromogen that functions as a mobile phase. The carrier may be a liquid, gas, gel, etc., and may be selected to provide the desired performance (time for change of color, contrast between different areas, and sensitivity) of the chromogen. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide); etc. The carrier may also be a disinfectant or bactericidal composition. The amount of the carrier and chromogen in the treatment composition may generally vary based on the level of microbe sensitivity and color pattern or design utilized. For instance, in some embodiments, the chromogen may be present in the treatment composition at a concentration from about 0.1 to about 100 milligrams per milliliter of carrier, in some embodiments from about 0.5 to about 60 milligrams per milliliter of carrier, and in some embodiments, from about 1 to about 40 milligrams per milliliter of carrier.

Besides the chromogen and carrier, the treatment composition may also contain a variety of other components. In one embodiment, for instance, additives are incorporated into the treatment composition that enhance the performance of the chromogen. For example, cyclodextrins may enhance the sensitivity of the chromogen and the contrast between regions that regions of different color. While not wishing to be bound by theory, the present inventors believe that such additives may inhibit the crystallization of the dye and thus provide a more vivid color and also enhance detection sensitivity. That is, single dye molecules have greater sensitivity for microbes because each dye molecule is free to interact with the microbial membrane. In contrast, small crystals of dye have to first dissolve and then penetrate the membrane. Examples of suitable cyclodextrins may include, but are not limited to, hydroxypropyl-β-cyclodextrin, hydroxyethyl-β-cyclodextrin, γ-cyclodextrin, hydroxypropyl-γ-cyclodextrin, and hydroxyethyl-γ-cyclodextrin, which are commercially available from Cerestar International of Hammond, Ind.

Surfactants may also help enhance the sensitivity of the chromogen and the contrast between different regions. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

In some embodiments, the treatment composition may also contain a binder to facilitate the immobilization of the chromogen on the desired substrate. For example, water-soluble organic polymers may be employed as binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

The treatment composition may be directly applied to the elastomeric article or applied via the use of an indicator strip. An indicator strip, for example, may contain a substrate that is applied with the treatment composition and subsequently placed into contact with the elastomeric article. Any of a variety of well-known application techniques may be employed for use in the present invention. Suitable application techniques include printing, dipping, spraying, melt extruding, coating (e.g., solvent coating, powder coating, brush coating, etc.), and so forth. Upon application, the treatment composition is dried to remove the carrier and leave a residue of the chromogen for interacting with a microbe. For example, the treatment composition may be printed onto a surface of the substrate to signal the presence of microbes upon a change in color. The treatment composition may cover all or only a portion of the substrate surface. In one embodiment, for example, the treatment composition is printed in the form of indicia that conveys a certain message to the user.

The substrate may be formed from any of a variety materials capable of being applied with the treatment composition. For example, the substrate may be formed from film, paper, a nonwoven fabric, a knitted fabric, a woven fabric, foam, etc. In one particular embodiment, the substrate is a facestock material commonly employed in the manufacture of labels, such as paper, polyester, polyethylene, polypropylene, polybutylene, polyamides, etc. An adhesive, such as a pressure-sensitive adhesive, heat-activated adhesive, hot melt adhesive, etc., may be employed on one or more surfaces of the facestock material to help adhere it to the elastomeric article. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns). A release liner may also be employed that contacts the adhesive prior to use. The release liner may contain any of a variety of materials known to those of skill in the art, such as a silicone-coated paper or film substrate. During use, the treated substrate and adhesive are peeled from the release liner. Thereafter, the adhesive is placed adjacent to the elastomeric article in the desired location to expose the treated substrate to the environment.

Generally speaking, the indicator strip may be applied to any portion of an elastomeric article desired so long as the chromogen is capable of contacting the microbe of interest during use. For example, the indicator strip may be applied to an outer, gripping surface of a glove so that the chromogen is able to contact microbes present in the environment in which the glove is used. Likewise, the indicator strip may be applied to the inner, donning surface of a glove so that the chromogen is able to contact microbes present on the user's hand. The indicator strip may cover an entire glove surface, a substantial portion of a glove surface, or only a small portion of a glove surface. Further, the indicator strip may have a variety of different shapes, such as circular, square, rectangular, ovular, triangular, dotted, etc. If desired, multiple indicator strips may also be employed and positioned at various locations of the elastomeric article.

Referring to FIG. 1, for example, one embodiment of a glove 20 is shown that may be placed on the hand of a user 22. The glove 20 has an outer, gripping surface 31 and an inner, donning surface (not shown) defined by an elastomeric material. The elastomeric material has finger regions 21, a palm side 27, and a top side (not shown). In the illustrated embodiment, an indicator strip 29 containing the chromogen is located on the outside surface 31 of the glove 20 and formed over the palm side 27. In this manner, the chromogen is located on the surface most susceptible to microbial contamination during use. Although the discussion above refers to the application of the treatment composition to the article, it should be understood that additives may also be applied separately from the chromogen-containing treatment composition.

Besides using an indicator strip, the present invention also contemplates embodiments in which the treatment composition is directly applied to the elastomeric article using any of a variety of application techniques such as described above. For example, in one embodiment, the treatment composition is dip-coated or sprayed onto one or more surfaces of the elastomeric article. Likewise, the treatment composition may also be incorporated within the matrix of the elastomeric article. For example, in some embodiments, the chromogen may be included within the coagulant, latex, coating, or other material used to form the article. In this manner, the chromogen will become uniformly distributed throughout the elastomeric material upon formation of the article. In certain cases, the chromogen may be used as a substitute for pigments and/or dyes used in commercially available elastomeric articles. For example, the chromogen may be used as a substitute for the pigment of the Safeskin® Purple Nitrile™ or Safeskin® Neon Nitrile™ gloves available from Kimberly-Clark, Inc. Of course, the chromogen may also be used in conjunction with other steps of elastomeric article-forming processes, such as being incorporated into silicone emulsions and/or surfactant solutions that are often coated onto surfaces of elastomeric articles.

Regardless of the manner in which it is applied, the amount of the chromogen employed is effective to result in a detectable color change upon contact with one or more microbes. The exact quantity may vary based on a variety of factors, including the sensitivity of the chromogen, the presence of other additives in the treatment composition, the desired degree of detectability (e.g., with an unaided eye), the concentration of the microbe, the intended application, etc. In some cases, it is desirable to only detect the presence of a microbe at concentrations that are considered pathogenic. For example, in food-based applications, a bacteria load of $1 \times 10^3$ colony forming units ("CFU") per milliliter of stock may be considered a threshold safety level. In such embodiments, the chromogen may be present at in an amount sufficient to only detect bacteria loads greater than $1 \times 10^3$ CFU per milliliter. Likewise, the amount of chromogen is generally low enough so as not to adversely impact the strength and stretch characteristics of the article. Although the actual amount may vary as described above, the chromogen is typically present in an amount from about 0.001 wt. % to about 20 wt. %, in some embodiments from about 0.01 wt. % to about 10 wt. %, and in some embodiments from about 0.1 wt. % to about 5 wt. % based on the dry weight of the elastomeric article. The amount of other additives (e.g., cyclodextrins, surfactants, binders, etc.) may also vary as desired, such as from about 0.001 wt. % to about 10 wt. %, in some embodiments from about 0.01 wt. % to about 5 wt. %, and in some embodiments from about 0.025 wt. % to about 1 wt. % based on the dry weight of the elastomeric article.

It should be understood that one or more additives, such as those described above, may be applied to the substrate and/or elastomeric article separately from the treatment composition. In one particular embodiment, an additive is separately applied to inhibit false positive readings. For example, some bleach compounds (e.g., sodium hypochlorite, chlorine, and sodium bisulfite) might cause a color change in the chromogen even when microbes are absent. Thus, if desired, a bleach indicator may be applied to the elastomeric article to signal the presence of bleach. One example of such a bleach indicator is 2,2',5,5'-tetramethyl benzidine, which is normally colorless and turns red when exposed to chlorine or sodium hypochlorite. The bleach indicator may also be a combination of starch and iodine, which turns black in the presence of chlorine or hypochlorite. Yet another bleach indicator, fuchsine, may be used to detect sulfites (e.g., sodium metabisulfite). Fuchsine is pink and changes to colorless when exposed to sulfites. In this way, regions of the elastomeric article may be designated as sensitive to microbes and other regions as sensitive to bleaches so that surfaces containing active bleach give color change combinations that allow the user to distinguish microbe contamination from bleach. The bleach indicator may be printed in a pattern to spell the word "BLEACH" so that if the article contacts bleach, "BLEACH" would become visible along with any other color change that the bleach may cause to the chromogen. The amount of bleach indicator may be an amount sufficient to cause a detectable color change.

As mentioned above, elastomeric articles are sometimes subjected to sterilization procedures prior to use. In such cases, any pre-applied chromogen may have already contacted one or more microbes and changed color. Upon sterilization, however, the microbes that caused the color change are typically eliminated. Thus, in some embodiments of the present invention, the chromogen may be sealed from the environment to inhibit the likelihood of premature color change prior to sterilization. For example, a treatment composition containing the chromogen may be sealed within a container or bottle. When it is desired to use the chromogen, such as after sterilization, the contents are removed and applied to the elastomeric article, such as by spraying. In another embodiment, an indicator strip containing the chromogen may be sealed within a package formed from a liquid-impermeable and/or vapor-impermeable film. To use the indicator strip, the package is simply opened, and the indicator strip is removed and placed on the elastomeric article.

In other embodiments, any color change of the chromogen that occurs prior to sterilization may possibly be reversed. The color change occurring in many types of solvatochromic dyes, for instance, is reversible at increased pH values. In this regard, some examples of basic pH modifiers that may be used to increase pH include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. Such a pH modifier may be added in any effective amount needed to achieve the desired color change.

As a result of the present invention, it has been discovered that microbial contamination of an elastomeric article may be readily detected through the use of a chromogen that undergoes a change in color in the presence of one or more microbes. One particular benefit of the present invention is that the color change may be visually observed within a relatively short period of time. For example, the chromogen may undergo a detectable color change in less than about 30 minutes, in some embodiments less than about 5 minutes, in some embodiments less than about 1 minute, in some embodiments less than about 30 seconds, and in some embodiments, less than about 10 seconds. In this manner, the chromogen may provide a "real-time" indication of the presence or absence of microbes on the elastomeric article.

In addition, the chromogen may also provide information regarding the quantity of a microbe to which it is exposed. For example, the color change of the chromogen may be visually compared to a color obtained at known microbe concentrations to approximate the microbe concentration. Alternatively, color intensity may also be measured to quantitatively or semi-quantitatively determine the amount of a microbe. In one embodiment, color intensity is measured as a function of absorbance, with an increased absorbance generally representing an increased amine concentration. For example, absorbance readings may be measured at a wavelength of 650 nanometers using a microplate reader from Dynex Technologies of Chantilly, Va. (Model # MRX). In another embodiment, color intensity and change may be measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still other suitable devices for measuring the intensity of a visual color may also be used in the present invention. For example, one suitable reflectance reader is described in U.S. Patent App. Pub. No. 2003/0119202 to Kaylor, et al., which is incorporated herein in its entirety by reference thereto for all purposes.

Regardless of the manner in which color intensity is measured, the result may be compared with a predetermined detection curve in which the color of the chromogen is plotted versus various known concentrations of a microbe. In this manner, the color of the chromogen may be measured during use and readily correlated to a microbe concentration for providing quantitative or semi-quantitative results to a user. In addition, the color change may occur rapidly in accordance with the present invention. For example, the chromogen may begin to change color in less than about 1 minute, in some embodiments less than about 30 seconds, and in some embodiments, less than about 10 seconds.

The present invention may be better understood with reference to the following examples. Although not all of the recited examples directly involve the presence of a microbe-sensitive chromogen on an elastomeric article, such examples nevertheless illustrate the ability of a microbe-sensitive chromogen to undergo a detectable color change in the presence of one or more microbes.

EXAMPLES

Materials Employed

All reagents and solvents used in the Examples were obtained from Sigma-Aldrich Chemical Co., Inc. of St. Louis, Mo. unless otherwise noted and were used without further purification. The following microorganisms were tested:

1. Gram negative (viable)
Escherichia coli (ATCC #8739).
Psuedomonas aeruginosa (ATCC #9027)
Salmonella choleraesuis
Gardnerella vaginalis
2. Gram positive (viable)
Staphylococcus aureus (ATCC #6538)
S. Xylosis
Lactobacillus acidophilus
3. Gram positive (dead)
Staphylococcus Aureus (ATCC #6538)
S. Xylosis
4. Yeast (viable)
Candida Albicans
5. Mold (viable)
Aspergillus Niger
6. Viruses
Polio virus type 1
Herpes Simplex virus 1 (HSV-1)
Rhinovirus
Measles
Vaccinia
Influenza A All viruses were obtained from Gibraltar Laboratories, Inc. of Fairfield, N.J. Reichardt's dye and 1-docosyl-4-(4-hydroxstyryl)-pyridinium bromide were also obtained from Sigma-Aldrich Chemical Co, Inc.

Example 1

Figure 2:
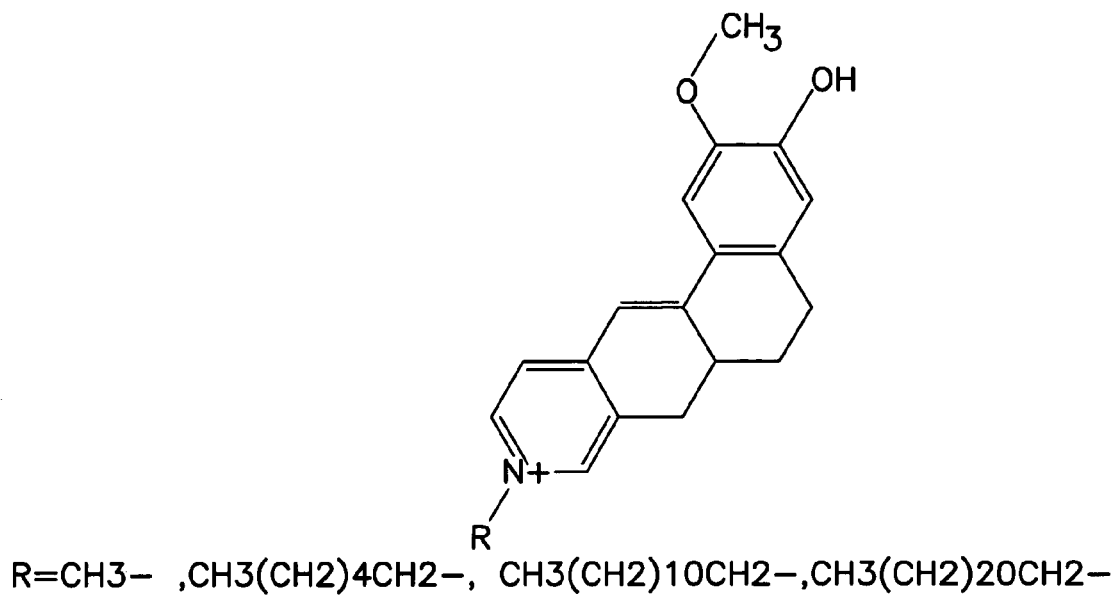
FIG. 2 is the structure of one merocyanine dye that may be used in the present invention.
Figure 3:
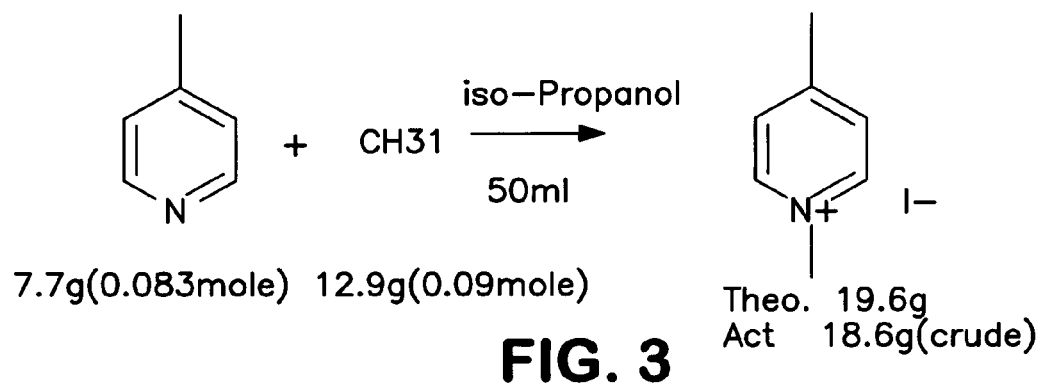
FIGS. 3-4 illustrate one method for synthesizing a merocyanine dye.

The ability to form merocyanine dyes for use in the present invention was demonstrated. For example, the merocyanine dye shown in FIG. 2 was synthesized in the laboratory using a two-step reaction. Specifically, as shown in FIG. 3, methyl iodide was added slowly to a stirred solution of δ-picoline in 50 milliliters of isopropanol in an ice bath. After addition was complete, the reaction was heated to reflux and reflux continued for 2 hours. The solution was then chilled in an ice-bath and the precipitate filtered, and washed with chilled alcohol, on a Buchner funnel. The powder was then dried in the fume-hood for 2 hours.

Figure 4:
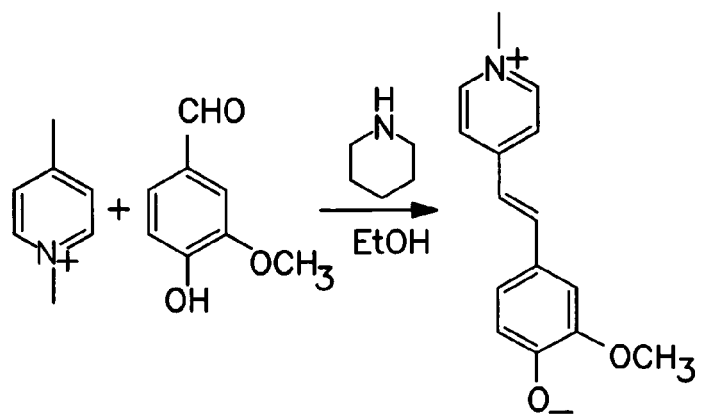

Yield of crude product was 18.6 grams. The crude product was not further purified and used directly for the next step. N-methyl-δ-Picolone (9.4 grams, 0.04 moles), and vanillin (6.1 grams, 0.04 moles) were all dissolved into 50 milliliters of ethanol with stirring as shown in FIG. 4. To this solution was added piperidine (3.4 grams, 0.04 mole) and the mixture refluxed for 16 hours. The reaction mixture was then chilled in an ice-bath and the product filtered off using a Buchner funnel and washed with chilled ethanol. The crude dye of structure 13 was obtained, where R is methyl. The dye was then stirred in 250 milliliters of 0.2 Molar potassium hydroxide solution for 60 minutes to form the zwitterion and then filtered off using a Buchner funnel. The dye was then crystallized from the minimum quantity of a 1:1 water/methanol mixture. The yield was 9.4 grams (98%).

Other merocyanine dyes were also synthesized in a similar manner by selecting an alkyl group of the alkyl iodide to correspond with the desired respective "R" group for the dye. The following Table 1 shows the compounds and the yields obtained for dye structure 13 for three different R groups.

TABLE 1

Alkyl Derivatives Synthesized and the Yields Obtained

| "R" Group | Yield (%) |
| --- | --- |
| Methyl | 98 |
| Hexyl | 92 |
| Dodecyl | 87 |

Example 2

The ability to apply a chromogen to an elastomeric glove in accordance with the present invention was demonstrated. Specifically, a solution of Reichardt's dye (160 milligrams per 10 milliliters of acetonitrile) was brushed onto a piece of a natural rubber latex glove (commercially available from Kimberly-Clark Corp.). A 100-microliter drop of $10^7$ CFU/mL *S. aureus* was then applied to the surface of the glove and gently spread using a disposable pipette. Thereafter, a finger of a second natural rubber latex glove (commercially available from Kimberly-Clark Corp.) was dipped into a solution of Reichardt's dye (160 milligrams per 10 milliliters of acetonitrile). After drying, the fingers of the second glove were used to spread bacteria from the *S. aureus* droplet placed onto the piece of latex glove to another area on the latex piece. The color of both the glove piece and the glove finger immediately changed. Similar results were also achieved for vinyl and nitrile gloves (commercially available from Kimberly-Clark) treated with the Reichardt's dye solution in the manner described above.

Example 3

The ability to use isopropanol as a carrier for the chromogen was demonstrated. Plastic doorknobs were utilized as a "real world" surface on which to test bacterial contamination. A raw chicken leg was initially aged at room temperature for several days to ensure high bacterial levels (referred to hereinafter as "aged chicken"). Juice from the aged chicken was then used to mark the surface of one of the knobs. The other door knob was left uncontaminated as a control. Both knobs were wiped. Reichardt's dye was then dissolved in isopropanol (160 milligrams dye into 10 milliliters of isopropanol). The isopropanol solution of the dye was sprayed on both surfaces. The contaminated area of the doorknob was easily observed by its color change of the Reichardt's dye from blue to colorless.

Example 4

The ability to titrate various concentrations of bacteria with dye was demonstrated. 100 microliters of serially diluted *S. aureus* bacterial suspensions were placed onto a SCOTT® paper towel. Drops (10 microliters) of the Reichardt's dye in acetonitrile solution (40 milligrams/10 milliliters) were then pipetted onto each spot where the bacteria was placed. The dye solution changed color in less than 1 second. Additional drops were placed on the same spot until the dye color remained steady and the purple/blue color did not fade. This was repeated on each spot corresponding to where different concentrations of bacteria were placed. The results showed a good correlation to the level of bacterial contamination on a surface.

Example 5

The ability to titrate various concentrations of bacteria with dye was demonstrated. A sample of aged, pooled female urine (100 microliters) was placed on a cellulosic towel to yield several spots each having 100-microliter volumes of the urine. Aged female urine is known to have high bacterial contamination and the results show a high level of contamination. Two solutions of Reichardt's dye were used for a titration study: 40 milligrams dye/10 milliliters acetonitrile and 160 milligrams dye/10 milliliters acetonitrile. The dye solutions were then placed onto the urine spots in 10-microliters aliquots and continued until the blue/purple dye color remained (that is, dye was added to the urine until the color persisted). Table 2 presents the volume of each dye solution required for the dye color to remain steady.

TABLE 2

Bacterial Quantification of Female Pooled Urine

| Sample | 4 mg/ml Dye Solution | 16 mg/ml Dye Solution |
|---|---|---|
| Urine | 120 microliters | 30 microliters |

Example 6

In the same manner as described in Example 5, bacteria and other microorganisms were pipetted onto a cellulosic towel. $10^7$ CFU/milliliters of *S. aureus*, *C. albicans* (yeast), *G. vaginalis*, *E. coli*, *P. aeruginosa*, and *L. acidophilus* were pipetted onto the towel (100 microliters each). In addition, $10^5$ of *A. niger* (a common mold) was also pipetted onto the towel. Reichardt's dye solution (160 milligrams in 10 milliliters of acetonitrile) was then added in 10-microliter aliquots to each spot and the numbers of drops needed to establish a persistent color were counted. The amount of dye required to maintain a persistent purple color for each organism is provided in Table 3.

TABLE 3

Titration of Various Microorganisms with Reichardt's Dye

| Compound | Type | Amount of Dye Required for Persistent Color (μl) |
|---|---|---|
| Lactobacillus | Gram(+) | 110 |
| S. aureus | Gram(+) | 90 |
| G. vaginalis | Gram(−) | 90 |
| E. coli | Gram(−) | 80 |
| P. aeruginosa | Gram(−) | 80 |
| C. albicans | yeast | 70 |
| A. niger | Mold | 50 |

The strongest reaction was observed with *L. acidophilus*, followed by *S. aureus*, *G. vaginalis*, *E. coli*, *P. aeruginosa*, *C. albicans*, and finally *A. niger*. Although there seemed to be as strong a reaction for the gram-positive *S. aureus* as for the gram-negative *G. vaginalis*, the amounts required to reach a steady-state reaction were different for various types of bacteria and pathogens.

Example 7

The mechanism for the detectable color change was investigated. Onto a SCOTT® paper towel were placed solutions of *E. coli*-derived detoxified lipopolysaccharide (Lipid A component removed), lipoteichoic acid derived from *Streptococcus faecalis*, *E. coli*-derived lipopolysaccharide, and muramic acid. With the exception of the pure LPS, all solutions were prepared in 5% (wt/wt), 1% (wt/wt), and 0.2% (wt/wt) concentrations. Pure LPS was prepared in 0.1% (wt/wt), 0.02% (wt/wt), and 0.004% (wt/wt). Reichardt's dye (160 milligrams in 10 milliliters acetonitrile) was added in 10-microliter aliquots to each spot and the amount of dye required to produce a persistent color was recorded. The reverse experiment was also conducted where the cell-wall compounds were placed onto a spot of dye on the paper towel. Muramic acid produced the strongest reaction, resulting in a near instantaneous color change of the dye in both experimental set-ups. The other compounds did cause eventual color change of the dye, but did not appear to react as strongly as muramic acid. Because muramic acid is found in greater concentrations on gram-positive bacteria, these results demonstrate the potential of this dye to not only give CFU per milliliter data, but also the potential to distinguish between gram-positive and gram-negative bacteria based on strength and speed of reaction.

Example 8

The ability of Reichardt's dye to respond to certain components of chicken fluid, such as lipids and proteins, was demonstrated. Canned chicken broth was utilized as a control that would contain chicken derived products such as lipids, protein, etc., to check for potential interferences from these naturally occurring materials. Freshly opened Swanson® Chicken Broth was pipette onto a hot plate surface and wiped dry with a SCOTT® towel. Juice from raw chicken that had been stored at room temperature for several days was also pipetted onto the hot plate and wiped dry as a positive control. The Reichardt's dye indicator (160 milligrams in 10 milliliters of isopropanol) was sprayed over the surface and it was clear that only the side containing the aged chicken juice (and thus bacteria) changed color. Thus, in the case of chicken, the presence of microbes was clearly responsible for triggering the change in color, and not some other component, such as chicken fat or proteins.

Example 9

The extent to which acid-base reduction contributed to the color change of Reichardt's dye in the presence of microbes was investigated. Several drops of Reichardt's dye (160 milligrams in 10 milliliters of acetonitrile) were pipetted onto a SCOTT® towel and allowed to dry. Two compounds known to cause color changes (acetic acid and Aldrich buffer at a pH of 2.0) were each dropped onto two of the spots, and led to rapid color change of the dye. A drop of 1 N NaOH was then pipetted onto one of each of the spots, causing rapid re-colorization. The blue/purple color of Reichardt's dye returned after the 1 N NaOH was added.

A second experiment was performed using the spray to corroborate these results. Aged raw chicken juice was pipetted onto the hot plate surface in an easily recognizable pattern. The surface was blotted dry and sprayed with Reichardt's dye (160 milligrams in 10 milliliters acetonitrile), causing color change of the dye in the exact form of the pattern of chicken juice. A drop of 1 N NaOH was then placed on an area that previously changed color, leading to re-colorization of that small spot. This was repeated with another area.

To test the possibility that the 1 N NaOH was simply acting on the bacteria and not the dye, aged chicken juice and 1 molar NaOH were mixed in equal proportions and allowed to stand for 30 seconds. This mixture was then used to create another identical (though smaller) pattern. This solution also caused rapid color change of Reichardt's dye, however, the color returned upon addition of 1 N NaOH.

Example 10

The ability of Reichardt's dye to respond to healthy (low pH, no bacterial infection), a pH positive/Bacterial Vaginosis (BV) (no bacterial infection, but higher than normal pH), and pH positive/BV positive (higher than normal pH and known bacterial infection) vaginal fluid samples was demonstrated. A sheet of stickers was brush-coated with two different concentrations of Reichardt's dye solution (160 milligrams/10 milliliters acetonitrile, 80 milligrams/10 milliliters acetonitrile, 40 milligrams/10 milliliters acetonitrile, 20 milligrams/10 milliliters acetonitrile). A sticker of each concentration was tested with normal, BV positive/pH positive, and BV negative/pH positive vaginal fluid samples. Normal vaginal fluid yielded the sharpest color change of the dye, presumably due to the combination of *lactobacillus* and low pH. The BV positive/pH positive sample exhibited the next sharpest color change, perhaps due to the presence of large numbers of BV bacteria. The BV negative/pH positive sample only faintly changed the color of the dye, perhaps due to a lesser amount of *lactobacillus* than in the normal sample. The three states of color change were easily distinguishable.

Example 11

A solution of Reichardt's dye (80 milligrams/10 milliliters acetonitrile) and TWEEN® 80 (200 microliters) polyoxyethylene surfactant (from Fischer Scientific, Pittsburgh, Pa.) was prepared. This solution was then used to coat a ceramic surface and allowed to air dry. A second solution of Reichardt's dye (80 milligrams/10 milliliters acetonitrile) without surfactant was placed on the surface and allowed to air dry. After drying, a drop of aged chicken juice known to have a high bacterial count was placed on the each coating area. The area containing the TWEEN® 80 surfactant changed color at a much faster rate (less than 20 to 30 seconds) when compared to the area that did not contain the TWEEN® surfactant. Furthermore, the addition of TWEEN® surfactant allowed for easy removal of the dye from the surface. The addition of a small amount of water allowed for complete removal from the surface while the addition of water to the spot that did not contain the surfactant did not improve ease of removal from the surface.

Example 12

The behavior of Reichardt's dye coatings made using various different solvents was evaluated. Solutions of Reichardt's dye in acetonitrile, isopropanol, and xylenes were prepared and the solutions were used to coat SCOTT® kitchen rolls towels and allowed to air-dry. The treated towels had 100-microliter aliquots of *S. aureus* placed on them, and the coating was observed for a color change. Only the acetonitrile solution-based coating had a rapid color change where the bacterial suspension was placed. The Reichardt's dye was observed to have an even color when dissolved in acetonitrile. No visible color change was observed with the other two solvent coatings. However, the present inventors found that the concentration of Reichardt's dye could be adjusted such that isopropanol could be utilized as a solvent for the dye. Though the color of the dye was less intense than that seen with acetonitrile, the color change due to microbial contamination was still readily observed.

Example 13

The transparent film covering half of a fresh chicken on a polystyrene tray (from supermarket) was stored at room temperature for three weeks. The pale yellow juices that collected in the polystyrene tray were collected using a pipette and used for tests. 47 milligrams of 1-docosyl-4-(4-hydroxystyryl)-pyridinium bromide (an N-docosyl-merocyanine dye available from Aldrich Chemical) was mixed with 10 grams of dimethylformamide. A small amount of solids remained after shaking and allowing to settle. The orange supernatant fluid was dropped onto woven cotton fabric of basis weight (29.2 cm×20.3 cm=6.888 grams) to make orange-yellow colored circles. One drop of 1 N sodium hydroxide solution was added to one orange-yellow spot on the cotton fabric, changing the color from orange-yellow to a pinkish orange. Aged chicken juice was spotted onto the orange-yellow spots on the cotton fabric, producing a color change to very pale yellow. The color change was rapid on cotton. Similarly, aged chicken juice was dropped onto the pinkish-orange areas on the cotton (dye+NaOH soln.) causing a similar color change from pinkish-orange to very pale yellow.

Example 14

Female human urine was collected and stored for 24 hours at 37° C. Pooled female urine may be expected to have a bacterial loading of approximately $1\times10^5$ CFU/milliliters after storage under these conditions. N-methyl merocyanine dye was formed as described in Example 1, and 0.5 grams of the dye was then dissolved in 20 milliliters deionized water. The solution was coated onto a SCOTT® kitchen roll paper towel by dipping the towel into the solution by dipping the towel into the solution, allowing the excess to drip off, and then allowing the coated toweling to dry at ambient conditions. The paper towel was stained a deep orange color by the dye. The aged urine was dropped onto the orange colored towel to give an immediate color change from deep orange to pale yellow. As a control, the aged urine was filtered through a 0.2-micron filter to remove bacteria and other microbes. After filtration, the aged urine did not cause a color change when dropped onto the towel suggesting that microbes were responsible for causing the color change vs. other components in the aged urine.

Example 15

Budgerigar feces was collected from a caged pet budgie, and shaken in approximately 10 milliliters of Atlanta city domestic tap water. N-methyl merocyanine dye was synthesized as described in Example 1, and 0.5 grams of the dye was then dissolved in 20 milliliters deionized water. The solution was coated onto a SCOTT® kitchen roll paper towel by dipping the towel into the solution, allowing the excess to drip off, and then allowing the coated toweling to dry at ambient conditions. The paper towel was stained a deep orange color by the dye. Drops of the budgie feces suspension in tap water were spotted onto the coated towel and produced an immediate color change from deep orange to pale yellow where the suspension was added. As a control, tap water was dropped onto a different area of the towel and while the color was diluted somewhat by the water, the area remained orange.

Example 16

A SCOTT® paper towel was first coated with hydroxypropyl-beta-cyclodextrin (from Cerestar International, Hammond, Ind., USA) in solution in water (1 gram in 20 milliliters) by dipping and air-drying at ambient temperature. After drying, the coated paper towel was treated with a solution of Reichardt's dye in isopropanol (1 weight percent) and allowed to air-dry. The dried towel was a purple/blue in color. The present inventors believe that the cyclodextrin hindered the crystallization of the dye, thus allowing a more vivid color of the dye to occur on the paper towel. This coated towel was used in a test with gram-negative bacteria (*E. coli*) and found to turn colorless in less than 5 seconds when an aliquot of 100 microliters of media containing 10,000 CFU per milliliter was applied to the towel. This color change was found to occur down to the bacteria concentration of 500 CFU per milliliter, though this took as long as 15 seconds. The inventors believe that by careful use of a coating (e.g. cyclodextrin), a monolayer coating of the dye may be formed.

Example 17

A test using the Reichardt's dye coated paper towel with a "dry" bacteria sample was carried out. Specifically, a dry sample of a colony of *E. coli* bacteria was lifted off an agar petri dish that contained a series of growing cultures. This dry sample was then rubbed onto a pre-moistened dye coated SCOTT® paper towel. The area where the colony was placed and rubbed turned colorless within 1 to 5 seconds.

Example 18

A mixture of Reichardt's Dye and 3,3',5,5'-tetramethylbenzidine (TMB) was coated onto a SCOTT® paper towel and allowed to air-dry. A dilute bleach solution was applied to the paper towel which resulted in the Reichardt's dye de-colorizing and the TMB turning orange/yellow color. This shows that a bleach indicator may be used in conjunction with the chromogen. In the final test, a SCOTT® paper towel having a coating of Reichardt's dye and TMB chemistries was exposed to suspension of *E. coli* bacteria dropwise. The towel area that came in contact with the bacteria changed color to a white spot in less than 10 seconds. No orange/yellow color was observed to develop.

Example 19

Reichardt's dye was used without further purification. N-n-hexyl and N-n-dodecyl merocyanine dyes were synthesized as described in Example 1. Acetone, methanol, and acetonitrile solvents (HPLC grade) were obtained from Sigma-Aldrich Chemical Co., Inc. A Shimadzu UV-1601 UV-Visible Spectrophotometer (Shimadzu Corporation) was used to measure the longest wavelength peak absorption of the dyes in the range of 400 to 800 nanometers, dissolved in three different solvents, contained in quartz curvettes. The following table contains the results of the testing with the solvents on the left side and dyes across the top.

|  | Hexyl Merocyanine | Dodecyl merocyanine | Reichardt's dye |
| --- | --- | --- | --- |
| Acetone | 617.5 nm (Green) | 617 nm (Green) | 674 nm (Bluish-green) |
| Methanol | 514 nm (Orange) | 522 nm (Orange) | 509 nm (red) |
| Acetonitrile | 582 nm (Greenish-blue) | 600 nm (Blue) | 623 nm (Blue) |

The merocyanine dyes also showed absorption near 400 nanometers and longer wavelength absorption, which altered the perceived color. Based upon the spectroscopic measurements, these dyes showed large shifts (greater than 10 nanometers) in maximum wavelength peak absorption between these microbe-sensitive dyes when dissolved in different solvents.

Example 20

The ability of a chromogen to detect the presence of a virus in accordance with the present invention was demonstrated. Polio virus type 1, Herpes Simplex Virus 1 (HSV-1), Rhinovirus, measles, vaccinia, and influenza A were prepared and inoculated into MA-104 embryonic monkey kidney cells propagated and fed with Dulbecco's Modified Eagle's Medium (DMEM), supplemented with fetal calf serum to a concentration of 5% and incubated at 37° C.±1° C. in its presence of 5% $CO_2$ for 6 days. Viral propagation was detected by microscopic observation of infected cell sheets for cellular disintegration (cytopathic effect, CPE), such as rounding, crenation, lysis, pyknosis, etc., as observed in at least 50% of the cell sheet. Cytotoxicity was measured as the extent of cellular disintegration as produced by the agent alone without the virus. Virus was titrated using ten-fold serial dilutions in DMEM, 4 replicates MA 104 cultures per dilution, each replicate inoculated with 0.1 milliliters of virus dilution. The extent of viral replication was calculated as the tissue culture infectious dose-50% (TCID 50) as determined by the method of Reed and Muench.

Reichardt's dye-coated stickers (160 milligrams/10 milliliters acetonitrile, 80 milligrams/10 milliliters acetonitrile, 40 milligrams/10 milliliters acetonitrile, and 20 milligrams/10 milliliters acetonitrile) were used as a test surface. 50 microliters of undiluted virus ($TCID_{50}$ $10^{-8}$ Polio virus/mL; $TCID_{50}$ $10^{-7}$ HSV-1/mL; $TCID_{50}$ $10^{-7}$ Rhinovirus/mL; $TCID_{50}$ $10^{-6}$ measles virus/mL; $TCID_{50}$ $10^{-6}$ vaccinia/mL; and $TCID_{50}$ $10^{-7}$ influenza/mL) in media was dropped onto each sticker and allowed to stand for 3 minutes before removing the droplet with a cotton swab. For Rhinovirus and Poliovirus, which were diluted in both media and saline, aliquots of media alone, virus-free cell culture media, and virus-free cell culture saline were utilized as control samples and also allowed to stand for three minutes before swabbing. For the remaining viruses (which were used undiluted in their original culture media), only a media control was utilized.

For Polio virus, the saline control appeared to interfere with the dye, while the media did not cause color change. Dilutions of Polio virus in media were therefore used for the remainder of the experiment. The virus was diluted serially in media in ten-fold increments and 50-microliter aliquots applied to each sticker. After allowing to stand for 3 minutes, the droplets were swabbed off the sticker. For Rhinovirus, the media control was found to interfere, while the saline control did not lead to color change of the dye. Thus, ten-fold serial dilutions of the virus diluted in saline were applied to the stickers in 50-microliter aliquots and swabbed after 3 minutes. For Polio virus and Rhinovirus, the stickers changed color down to $10^{-6}$ (i.e. the sixth in the series of ten-fold dilutions), indicating that the dye-coated stickers possessed sensitivity towards the detection of these viruses (de-colorization slightly stronger for Polio virus). For HSV-1, Influenza A, measles, and vaccinia, only the 50-microliter droplets of (undiluted) virus were placed on the stickers. The subsequent de-colorization observed was compared to that observed for the virus-free control media and also to a *Salmonella* ($10^8$ CFU/mL) positive control. Though the de-colorization was not as strong as that observed for *Salmonella* bacteria, exposure to undiluted HSV-1 virus led to stronger de-colorization of the sticker than that observed for Rhinovirus and Polio virus. De-colorization in response to Influenza A, vaccinia, and measles viruses was less than that observed for the other viruses.

Two solutions of Reichardt's dye (80 milligrams/10 milliliters acetonitrile with or without 400 microliters TWEEN 80 surfactant) were also prepared. A 100-microliter drop of either Polio virus or Rhinovirus (both undiluted in media) was pipetted onto a folded SCOTT® paper towel and drops of the Reichardt's dye were added to each of the virus-containing spots. The color was rapidly discharged for both surfactant- and non-surfactant-containing solutions. Dye was eventually added until the color persisted (approximately 9 drops). The same media and saline controls mentioned previously were also tested. Though media did exhibit some ability to de-colorize the dye, the saline presented the same titration behavior previously observed with water.

Example 21

The ability of Reichardt's dye to provide quantitative information regarding the concentration of bacteria was demonstrated. A paper-based substrate (Neenah Bond™) (available from Neenah Paper, Inc. of Alpharetta, Ga.) was initially treated with a Reichardt's dye solution (80 milligrams/10 milliliters acetonitrile) by dipping the paper in the coating or brushing the coating on the paper, and thereafter hanging the paper to dry. Seven (7) drops of known concentrations of *S. aureus* ($10^1$, $10^2$, $10^3$, $10^4$, $10^5$, $10^6$, and $10^7$ CFU per milliliter) were placed on top of each sheet. After approximately 2 minutes, the drops were removed and blotted, revealing obvious color change at *S. aureus* concentrations of $10^5$ CFU/mL and above. The color differences at lower concentrations were less distinct, particularly for the brush-coated sheet.

A blind study was then conducted. For testing purposes, a first drop containing 100 microliters at a concentration of $10^6$ CFU/mL was placed on a portion of a dip-coated sheet containing Reichardt's dye. A second drop containing 100 microliters at a concentration of $10^5$ CFU/mL was placed on portion of a brush-coated sheet containing Reichardt's dye. Finally, a third drop containing *S. aureus* at a concentration of $10^4$ CFU/mL was placed on portion of a dip-coated sheet containing Reichardt's dye. Concentrations of these three drops were unknown to two of the experiment participants. After approximately 2 minutes, the drops were removed and blotted. Using the control regions, the concentrations of each sample were each visually estimated by these two persons. Both persons correctly estimated the concentration of the first sample to be $10^6$ CFU/mL. These persons also correctly guessed the concentration of $10^5$ CFU/mL for the second sample. The persons, however, incorrectly estimated the third sample to be $10^3$ CFU/mL. It is believed that this inaccuracy was due, at least in part, to the relatively low difference in color of the control regions at concentrations less than $10^5$ CFU/mL. The present inventors believe, however, that the concentration of the chromogen and uniformity of the coating may be readily selected to achieve accurate results at such low concentrations. In any event, because the control regions provided a more distinct color difference at higher concentrations (e.g., $10^5$ CFU/mL or above), it is believed that accurate results would be achieved at the more clinically relevant, high concentrations.

Example 22

The ability of Reichardt's dye to provide quantitative information regarding the concentration of bacteria was demonstrated. A paper-based substrate (Neenah Bond™) (available from Neenah Paper, Inc. of Alpharetta, Ga.) and a label (available from Avery-Dennison) were initially coated with a Reichardt's dye solution (80 milligrams/10 milliliters acetonitrile) and hung to dry. Aliquots (100 microliters) of known concentrations of S. aureus, P. aeruginosa, and E. coli were used to create control curves for each type of bacteria. More specifically, indicator strips coated with Reichardt's dye were exposed with decreasing amounts of the bacteria aliquots. A hand-held spectrophotometer was used to after application of each aliquot to determine "Delta E" value (calculated using $L^*$, $A^*$, and $B^*$ values) for each CFU/mL concentration. The results are set forth below in Table 4 (for paper) and Table 5 (for label).

TABLE 4

| | Results for Paper Substrates | | |
|---|---|---|---|
| log CFU/ml | Delta E (S. aureus) | Delta E (E. coli) | Delta E (P. aeruginosa) |
| 8 | — | 9.3642 | — |
| 7 | 11.73368 | 4.3483 | 4.9569 |
| 6 | 3.876455 | 3.2574 | 1.3193 |
| 5 | 2.447325 | 2.3320 | 1.7151 |
| 4 | 2.074175 | 3.0123 | 2.2358 |
| 3 | 1.866789 | 3.8228 | 1.7900 |

TABLE 5

| | Results for Label Substrates | | |
|---|---|---|---|
| log CFU/ml | Delta E (S. aureus) | Delta E (E. coli) | Delta E (P. aeruginosa) |
| 7 | 18.62321 | 7.778702 | 6.9567 |
| 6 | 6.908263 | 4.866590 | 4.2419 |
| 5 | 6.919863 | 4.643888 | 4.6519 |
| 4 | 4.791472 | 5.200596 | 4.9473 |
| 3 | 5.413890 | 5.130312 | 3.8787 |

Figure 5:
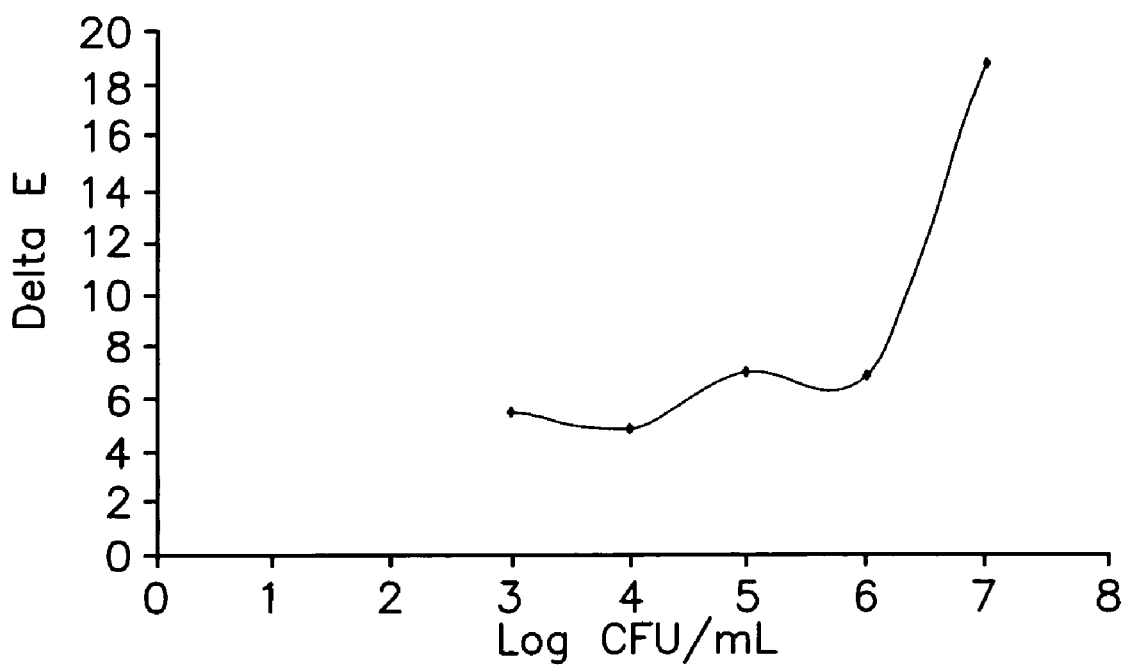
FIG. 5 is a graphical illustration of the results obtained in Example 22 in which Delta E is plotted versus known concentrations of *S. aureus*.
Figure 6:
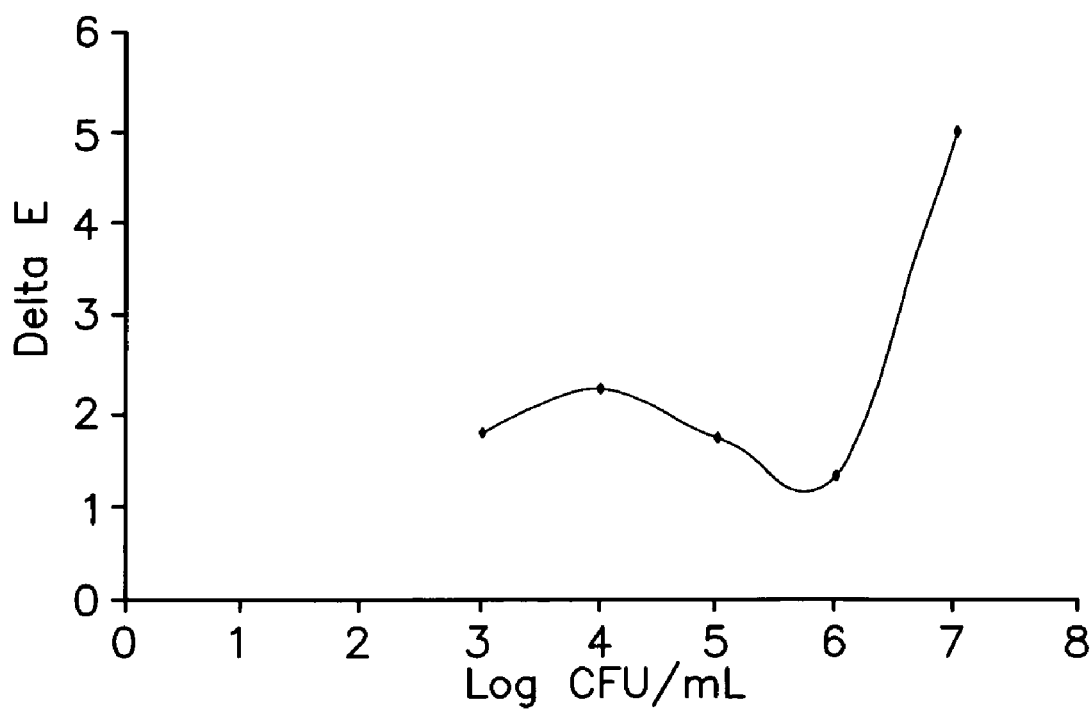
FIG. 6 is a graphical illustration of the results obtained in Example 22 in which Delta E is plotted versus known concentrations of *P. aeuruginosa*.
Figure 7:
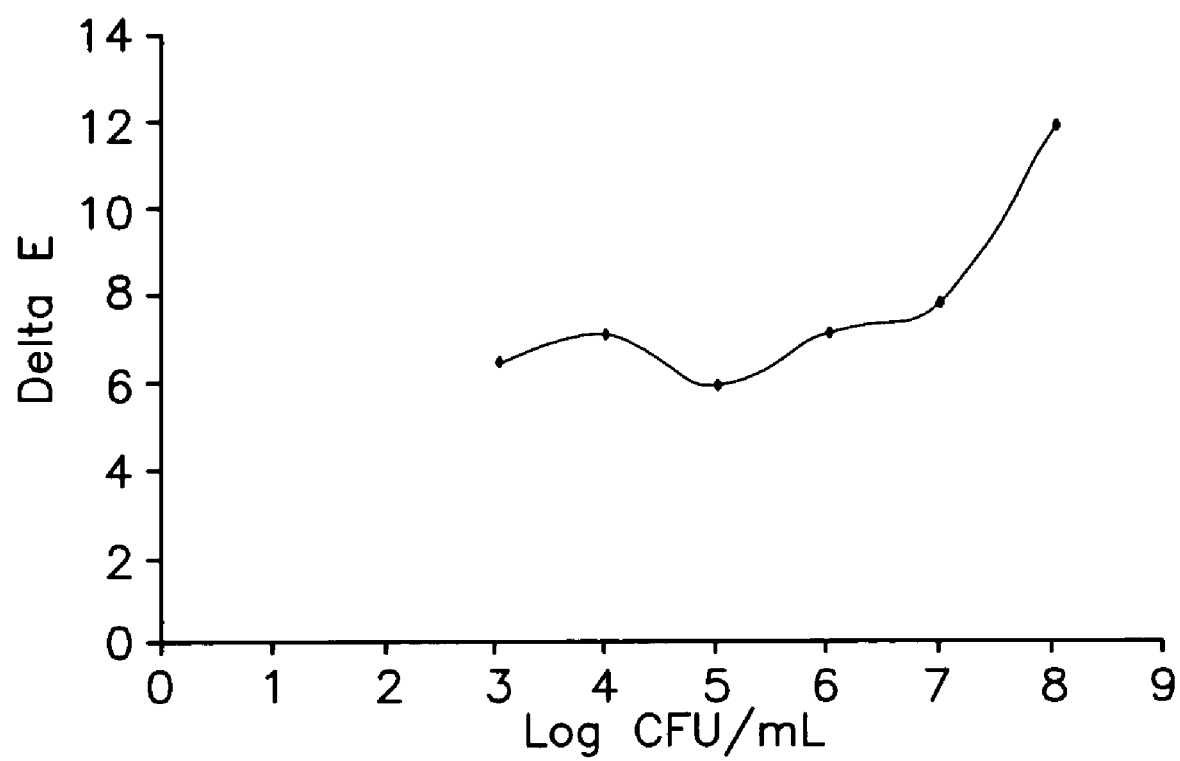
FIG. 7 is a graphical illustration of the results obtained in Example 22 in which Delta E is plotted versus known concentrations of *E. coli*.

From the above, standard detection curves were generated as shown in FIGS. 5-7 for S. aureus, P. aeruginosa, and E. coli, respectively. As shown, each type of bacteria changed the color of the dye-treated substrate in a slightly different way, creating a unique standard curve. Thereafter, drops of unknown bacteria concentrations were placed on the stickers and a spectrophotometer was used to measure the "Delta E" of the resulting color. The numerical values obtained for each unknown sample set forth below in Tables 6-7.

TABLE 6

| Results for Paper Substrates | | | | | | | | |
|---|---|---|---|---|---|---|---|---|
| S. aureus | | | E. coli | | | P. aeruginosa | | |
| log CFU/ml (actual) | Delta E | log CFU/ml (estimated) | log CFU/ml (actual) | Delta E | log CFU/ml (estimated) | log CFU/ml (actual) | Delta E | log CFU/ml (estimated) |
| 5 | 3.16136 | 5 | 3 | 1.3605 | 5 | 3 | 1.0267 | 5 |

TABLE 7

| Results for Label Substrates | | | | | | | | |
|---|---|---|---|---|---|---|---|---|
| S. aureus | | | E. coli | | | P. aeruginosa | | |
| log CFU/ml (actual) | Delta E | log CFU/ml (estimated) | log CFU/ml (actual) | Delta E | log CFU/ml (estimated) | log CFU/ml (actual) | Delta E | log CFU/ml (estimated) |
| 6 | 6.869068 | 5 to 6 | 7 | 7.1157 | 7 | 6 | 4.4954 | 5 to 6 |
| 6 | 4.228215 | 3 | — | — | — | 6 | 4.1002 | 3 to 6 |

As can be seen from the numerical data, the unknown concentrations were predicted by determining to which known Delta E value the Delta E value of the unknown was closest. Although a few of the results were not completely accurate, the present inventors believe that improving the uniformity of the coating would further enhance detection accuracy.

Comparative Example 1

The transparent film covering half of a fresh chicken on a polystyrene tray was stored at room temperature for three weeks. The pale yellow juices that collected in the polystyrene tray were collected using a pipette and used for tests. The aged chicken juice was dropped onto a SCOTT® paper towel. A solution of Cl Acid Green 41 was obtained from Aldrich Chemical that had a concentration of 0.008 moles per liter. Cl Acid Green 41 is a hydroxyanthraquinone dye having the following structure:

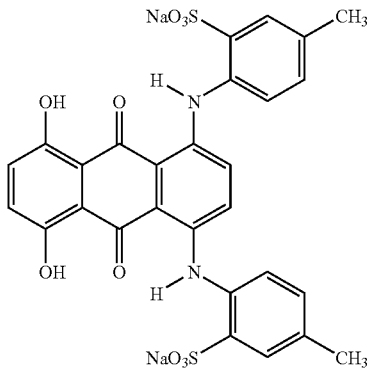

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

Comparative Example 2

The transparent film covering half of a fresh chicken on a polystyrene tray was stored at room temperature for three weeks. The pale yellow juices that collected in the polystyrene tray were collected using a pipette and used for tests. The aged chicken juice was dropped onto a SCOTT® paper towel. A solution of Cl Acid Green 25 was obtained from Aldrich Chemical that had a concentration of 0.008 moles per liter. Cl Acid Green 25 is an anthraquinone dye having the following structure:

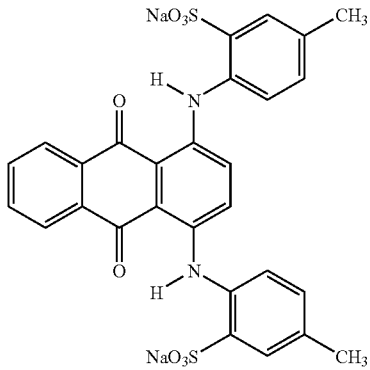

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

Comparative Example 3

The transparent film covering half of a fresh chicken on a polystyrene tray was stored at room temperature for three weeks. The pale yellow juices that collected in the polystyrene tray were collected using a pipette and used for tests. The aged chicken juice was dropped onto a SCOTT® paper towel. 50 milligrams of Acid Red 37 was obtained from Aldrich Chemical and dissolved in 10 milliliters of deionized water. Acid Red 37 is an aminoazo dye having the following structure:

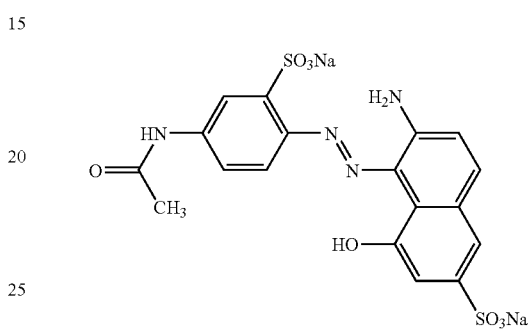

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

Comparative Example 4

The transparent film covering half of a fresh chicken on a polystyrene tray was stored at room temperature for three weeks. The pale yellow juices that collected in the polystyrene tray were collected using a pipette and used for tests. The aged chicken juice was dropped onto a SCOTT® paper towel. 50 milligrams of Acid Yellow 23 was obtained from Aldrich Chemical and dissolved in 10 milliliters of deionized water. Acid Yellow 23 is a phenylpyrazolone dye having the following structure:

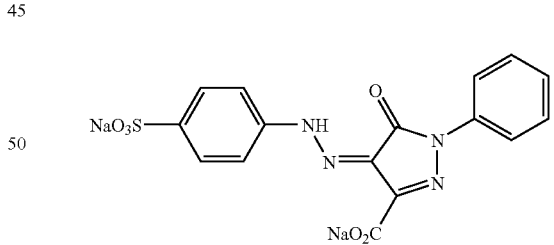

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

Comparative Example 5

The transparent film covering half of a fresh chicken on a polystyrene tray was stored at room temperature for three weeks. The pale yellow juices that collected in the polystyrene tray were collected using a pipette and used for tests.

The aged chicken juice was dropped onto a SCOTT® paper towel. An aqueous solution of Cl Acid Red 52 was obtained from Aldrich Chemical. Cl Acid Red 52 is a xanthene dye having the following structure:

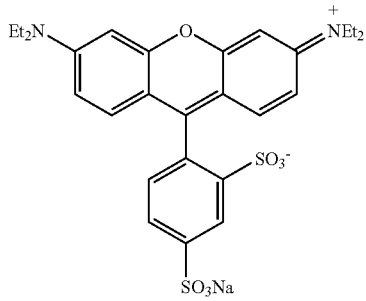

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

Comparative Example 6

The transparent film covering half of a fresh chicken on a polystyrene tray was stored at room temperature for three weeks. The pale yellow juices that collected in the polystyrene tray were collected using a pipette and used for tests. The aged chicken juice was dropped onto a SCOTT® paper towel. 30 milligrams of Cl Acid Blue 74 was obtained from Aldrich Chemical and dissolved in 10 milliliters of deionized water. Cl Acid Blue 74 is an indigoid dye having the following structure:

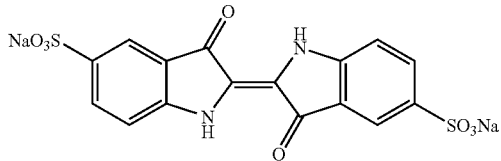

The dye solution was dropped onto the aged chicken juice. No color changes were observed. As a comparison, 100 milligrams of Reichardt's dye was also suspended in 10 milliliters of acetonitrile. Upon dropping this suspension onto the aged chicken juice, it immediately changed color.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastomeric glove comprising:
   an elastomeric material formed in the shape of a hand, the elastomeric material defining an inner donning surface and an outer gripping surface; and
   an N-phenolate betaine dye that undergoes a detectable color change in the presence of one or more microbes.

2. The elastomeric glove of claim 1, wherein the dye is contained within the elastomeric material.

3. The elastomeric glove of claim 1, wherein the dye is present on an indicator strip, the indicator strip being adhered to the inner donning surface and/or the outer gripping surface of the elastomeric glove so that the dye is capable of being exposed to one or more microbes.

4. The elastomeric glove of claim 1, wherein the dye is present on the outer gripping surface of the glove.

5. The elastomeric glove of claim 1, wherein the dye is present on the inner donning surface of the glove.

6. The elastomeric glove of claim 1, wherein the microbes are selected from the group consisting of bacteria, viruses, and fungi.

7. The elastomeric glove of claim 1, wherein the dye is Reichardt's dye.

8. The elastomeric glove of claim 1, wherein the dye is present in an amount of from about 0.001 wt. % to about 20 wt. % based on the dry weight of the elastomeric glove.

9. The elastomeric glove of claim 1, wherein the dye is present in an amount of from about 0.01 wt. % to about 10 wt. % based on the dry weight of the elastomeric glove.

10. The elastomeric glove of claim 1, wherein the color change occurs in less than about 5 minutes.

11. The elastomeric glove of claim 1, wherein the color change occurs in less than about 1 minute.

12. The elastomeric glove of claim 1, wherein the color change is reversible.

* * * * *